(12) United States Patent
Goldstein et al.

(10) Patent No.: US 10,950,359 B2
(45) Date of Patent: Mar. 16, 2021

(54) RADIATION SHIELD

(71) Applicant: Eco Cath-Lab Systems, Inc., Wilmington, DE (US)

(72) Inventors: James A. Goldstein, Royal Oak, MI (US); Remo J. Rossi, Sterling, MA (US); Kirk R. Dembek, Baldwinville, MA (US)

(73) Assignee: Eco Cath-Lab Systems, Inc., Wilmington, DE (US)

( * ) Notice: Subject to any disclaimer, the term of this patent is extended or adjusted under 35 U.S.C. 154(b) by 0 days.

(21) Appl. No.: 16/692,937

(22) Filed: Nov. 22, 2019

(65) Prior Publication Data
US 2020/0168353 A1    May 28, 2020

Related U.S. Application Data

(60) Provisional application No. 62/883,978, filed on Aug. 7, 2019, provisional application No. 62/883,466, filed
(Continued)

(51) Int. Cl.
*G21F 3/00* (2006.01)
*A61B 6/10* (2006.01)
(Continued)

(52) U.S. Cl.
CPC ............... *G21F 3/00* (2013.01); *A61B 6/107* (2013.01); *A61B 6/4441* (2013.01); *A61B 90/37* (2016.02);
(Continued)

(58) Field of Classification Search
CPC ... G21F 3/00; G21F 7/03; G21F 1/125; A61B 6/107; A61B 6/4441; A61B 6/4435; A61N 2005/1094
See application file for complete search history.

(56) References Cited

U.S. PATENT DOCUMENTS

| 7,057,194 B2* | 6/2006 | Goldstein | ................. G21F 3/00 |
| | | | 250/515.1 |
| 7,973,299 B2* | 7/2011 | Rees | ......................... G21F 3/02 |
| | | | 250/516.1 |

(Continued)

*Primary Examiner* — Brooke Purinton
(74) *Attorney, Agent, or Firm* — Harness, Dickey & Pierce, P.L.C.

(57) ABSTRACT

A radiation shield is adapted to be disposed transversely across a subject supported on the surface of a procedure table to protect medical professionals working in front of the radiation shield from radiation being applied to the subject behind the radiation shield. The radiation shield includes a movable barrier positional to extend transversely across a subject supported on the surface of a procedure table. The barrier has a generally vertically-oriented lower section; a generally forwardly sloping intermediate section; and a generally vertically-oriented upper section, forwardly offset from the plane of the lower section. A side section extends outwardly and rearwardly from one side of the lower, intermediate, and upper sections of the barrier. There is a recess in the lower edge of the lower section for accommodating a portion of the body of the subject on the surface of the procedure table, with portions of the lower section on each side of the recess projecting downwardly below the surface of the procedure table. A plurality of flexible radiopaque flaps depending from the perimeter of the recess block radiation from penetrating the gap between the subject and the perimeter of the recess.

19 Claims, 30 Drawing Sheets

Related U.S. Application Data on Aug. 6, 2019, provisional application No. 62/770,910, filed on Nov. 23, 2018.

(51) Int. Cl.
*A61N 5/10* (2006.01)
*G21F 7/03* (2006.01)
*A61B 6/00* (2006.01)
*A61B 90/00* (2016.01)

(52) U.S. Cl.
CPC . *A61B 2090/376* (2016.02); *A61N 2005/1094* (2013.01); *G21F 7/03* (2013.01)

(56) References Cited

U.S. PATENT DOCUMENTS

| | | | |
|---|---|---|---|
| 2010/0319713 A1* | 12/2010 | Byers | A61B 50/30 |
| | | | 128/853 |
| 2015/0272519 A1* | 10/2015 | Buchmeyer | A61B 6/04 |
| | | | 250/515.1 |
| 2016/0158082 A1* | 6/2016 | Gainor | A61G 7/05 |
| | | | 5/690 |
| 2016/0317110 A1* | 11/2016 | Rees | A61B 6/4423 |
| 2018/0249972 A1* | 9/2018 | Yifat | G01T 1/00 |

* cited by examiner

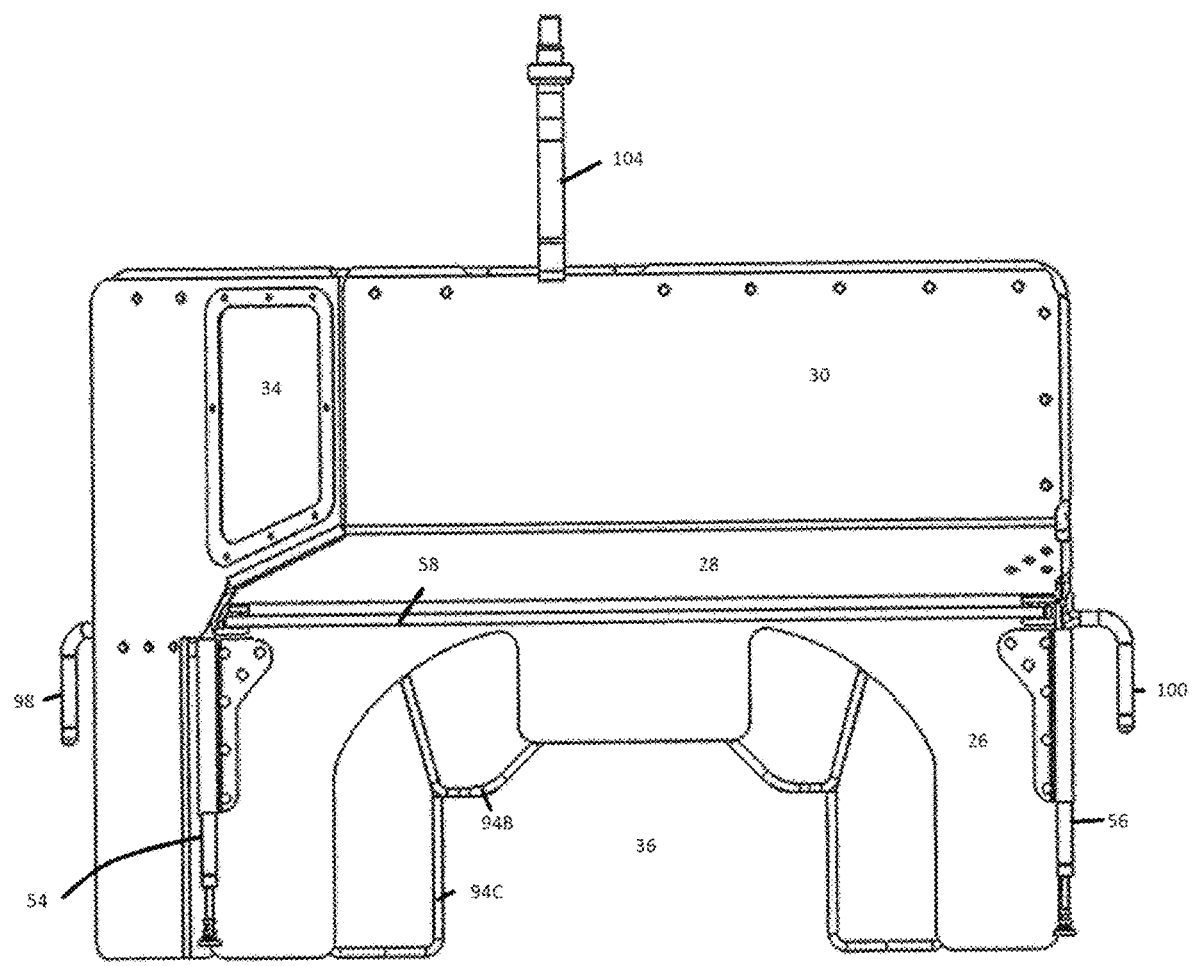
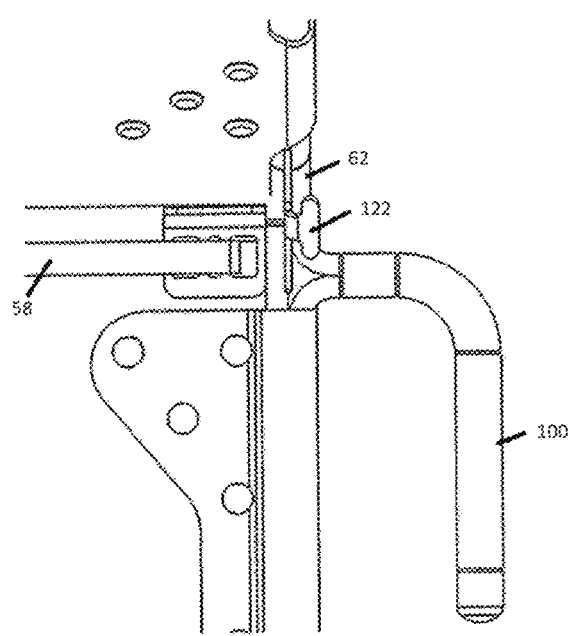
Fig. 10
Fig. 10A

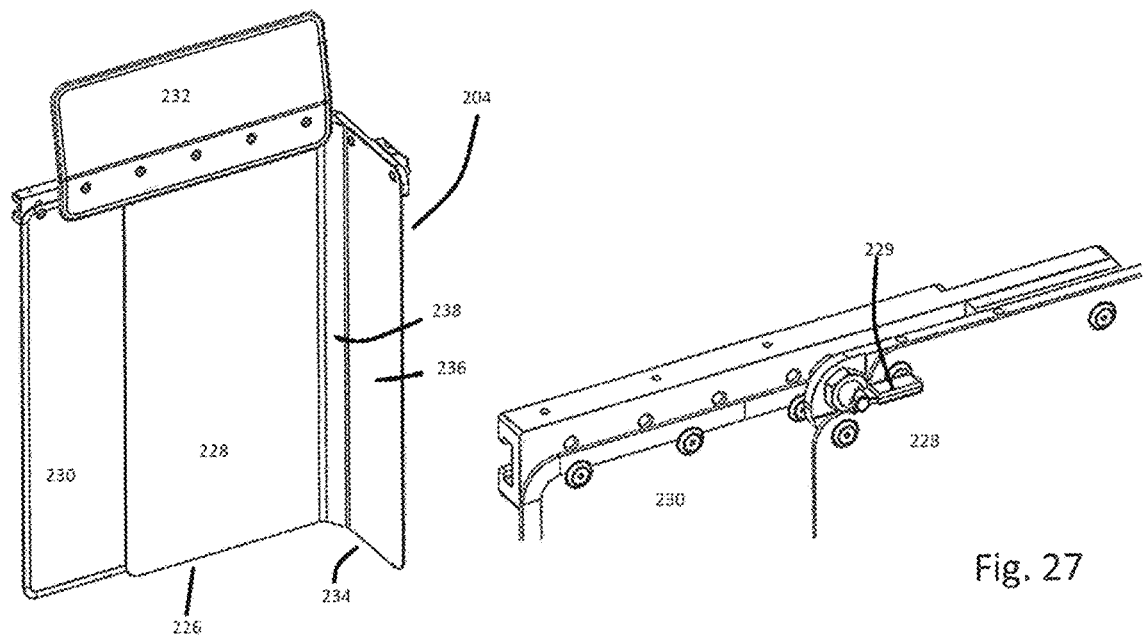
Fig. 26
Fig. 27
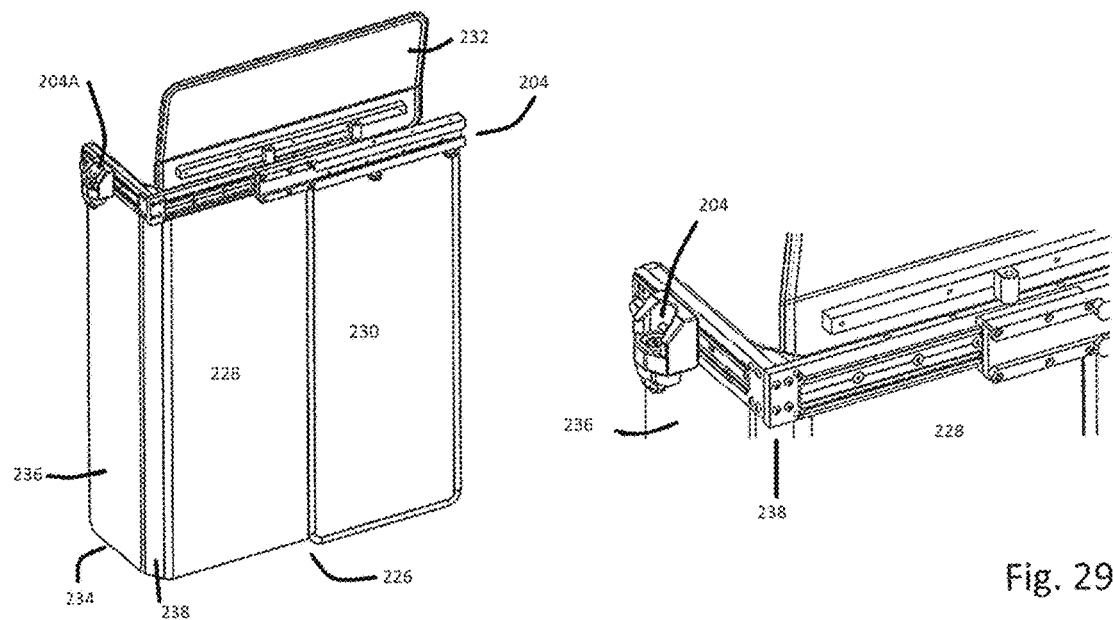
Fig. 28
Fig. 29

RADIATION SHIELD

FIELD

The present invention relates generally to radiation protection systems. More specifically, the present invention relates to methods for shielding persons (e.g., medical personnel) from radiation emitted by a radiation source during a radiologic procedure performed on a patient.

BACKGROUND

This section provides background information related to the present disclosure which is not necessarily prior art.

Radiographic equipment (e.g., x-ray equipment) is used when performing a wide variety of medical procedures. For example, radiographic equipment is used by cardiologists when positioning heart catheters in patients. Many procedures such as these require medical personnel to be in direct contact with the patient, thereby preventing the personnel from being in a separate room and potentially exposing the medical personnel to radiation. For this reason, radiation shields are used during radiographic procedures to reduce radiation exposure. Radiation shields typically are constructed of materials such as lead that significantly reduce the transmission of radiation. For example, some shields include lead plates mounted on stands that may be adjusted to position the plates between the medical personnel and sources of radiation. Despite the use of these shields, medical personnel are still exposed to radiation. Exposure comes from many radiation sources other than the primary source. For example, a significant secondary radiation source is radiation transmitted through the patient and even through the patient's extremities, to the medical personnel. Cumulative long-term radiation exposure may cause significant adverse effects to medical personnel. Medical personnel performing radiographic procedures typically spend many hours over their careers performing such procedures. Medical personnel typically wear protective clothing, including a full lead apron, a thyroid collar and leaded glasses, to reduce radiation exposure while performing the procedures. However, wearing heavy lead protective clothing may have long-term adverse effects, including disabling spinal disorders. Although there are many prior art radiation protection systems for protecting and shielding medical personnel from radiation exposure, these systems often require medical personnel to wear protective clothing. Therefore, there is a need for systems that reduce or eliminate the need for wearing protective clothing to reduce or eliminate the effects of wearing the protective clothing.

SUMMARY

This section provides a general summary of the disclosure, and is not a comprehensive disclosure of its full scope or all of its features.

Embodiments of the invention provide a radiation shield to protect medical personnel from radiation, such as radiation from medical imaging equipment, during medical procedures. A preferred embodiment of a radiation shield in accordance with the principles of this invention is adapted to be disposed transversely across a subject being supported by an upper support system and linked to connection points on the rail system of any procedure table to protect medical professionals working in front of the radiation shield from radiation being applied to the subject behind the radiation shield. This radiation shield preferably comprises a movable barrier, positionable transversely across a subject supported on the surface of a procedure table. The barrier preferably comprising a generally vertically-oriented lower section; a generally forwardly sloping intermediate section; and a generally vertically-oriented upper section, forwardly offset from the plane of the lower section. The barrier also comprises a side section extending outwardly and rearwardly from one side of the lower, intermediate, and upper sections. Transparent radiopaque window(s) can be provided in the barrier, for example in the side section and/or the upper section.

There is a recess in the lower edge of the lower section of the barrier for accommodating a portion of the body of the subject on the surface of the procedure table, with portions of the lower section on each side of the recess projecting downwardly below the surface of the procedure table. There are a plurality of flexible radiopaque flaps depending from the perimeter of the recess, for blocking radiation from penetrating the gap between the subject and the perimeter of the recess.

The barrier is preferably formed from a skeleton or frame, with a plurality of radiopaque panels mounted on the frame. These panels may be rigid or flexible, and they are preferably releasably mounted to the frame so that they can be removed for cleaning or replacement.

The height of the lower section of the barrier, and the slope of the intermediate panel are preferably such as to provide a vertical access space above a subject on the surface of the procedure table that is about 16 inches high, about 9 inches forward of the barrier. More preferably, the height of the lower section of the barrier, and the slope of the intermediate panel are such that a cylinder of about 12 inches in diameter, whose axis is about 10 inches in front of the plane of the lower section, could fit between the patient and the barrier. The top of upper section of the barrier is preferably at least about 36 inches above the surface of the procedure table. The side section preferably extends outward from the table center at least about 31 inches.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 9A is an enlarged side elevation view of the center of the shield show in FIG. 9;

FIG. 10 is a front elevation view of the preferred embodiment of the shield;

FIG. 10A is an enlarged front elevation view of handle on the right side of FIG. 10;

FIG. 26 is a perspective view of the lower shield assembly, showing the exterior side of the shield assembly opposite the physician station;

FIG. 27 is an enlarged partial perspective view of the lower shield assembly as shown in FIG. 26, showing the mounting of the telescoping panels;

Figures 24, 25:
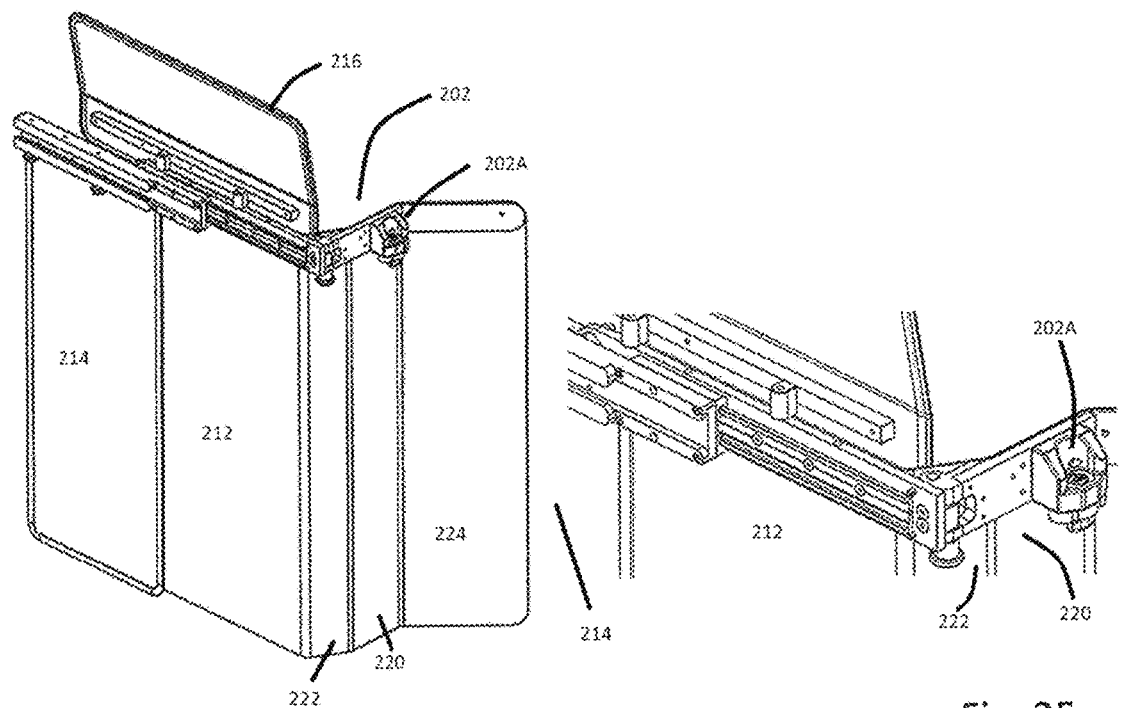
FIG. 24 is a perspective view of the lower shield assembly, showing the interior side of the shield assembly adjacent the physician station.
FIG. 25 is an enlarged partial perspective view of the lower shield assembly as shown in FIG. 24, showing the mounting of the telescoping panels.
Figure 30:
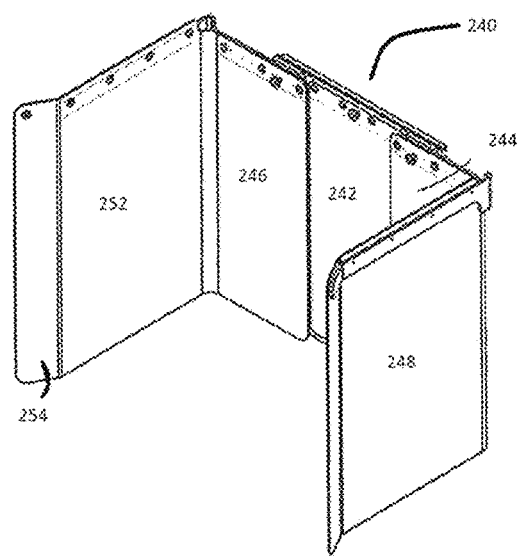
Figure 31:
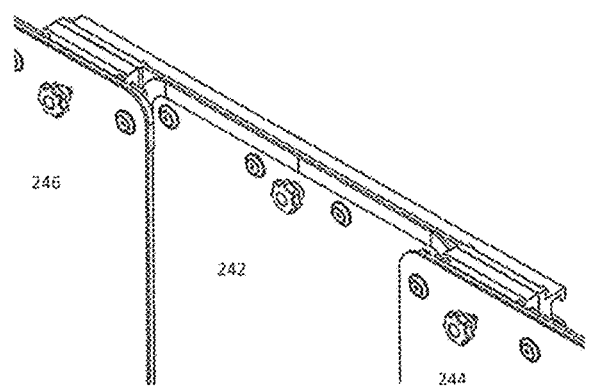
Figure 32:
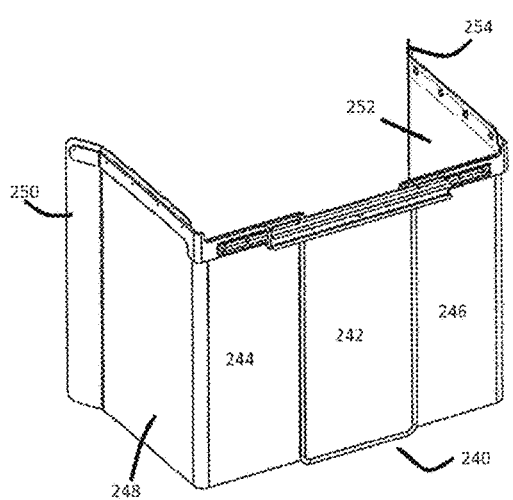
Figure 33:
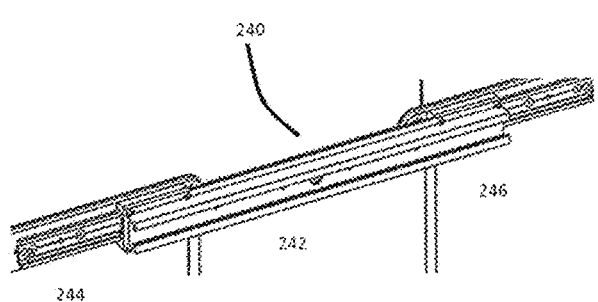
Figure 34:
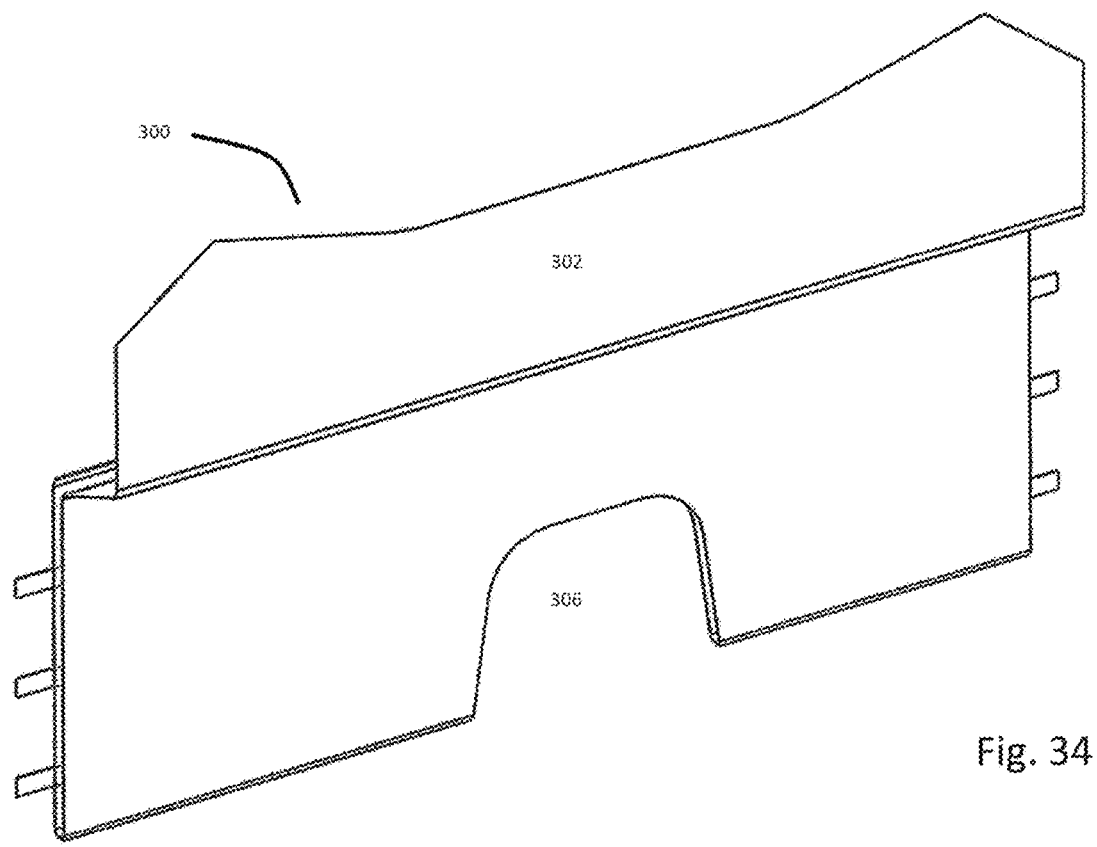
Figures 35, 36:
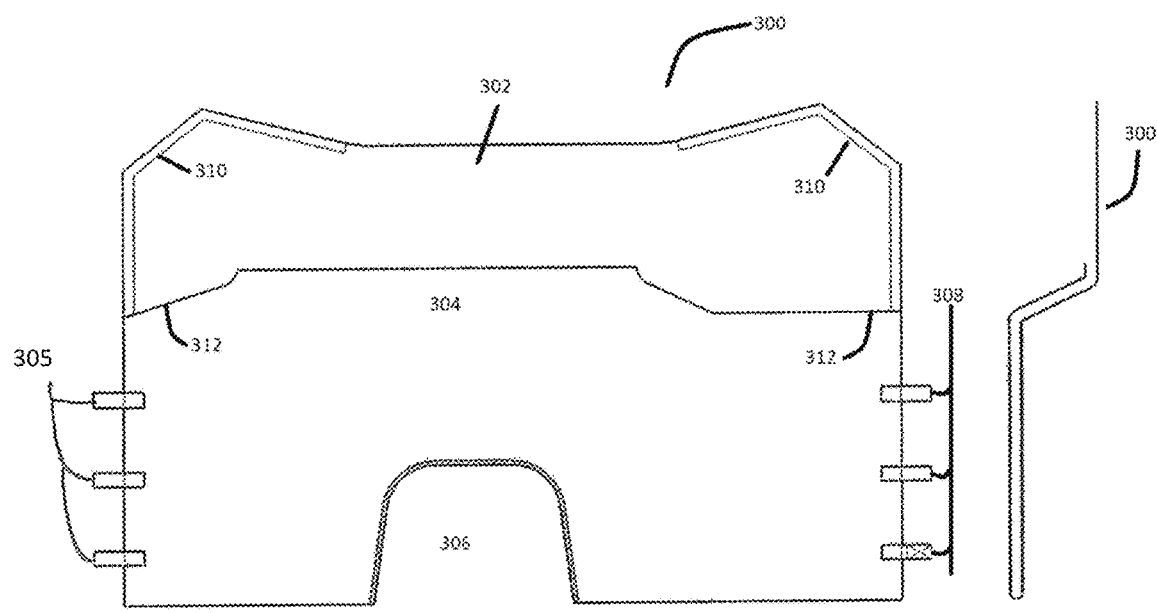
Figure 37:
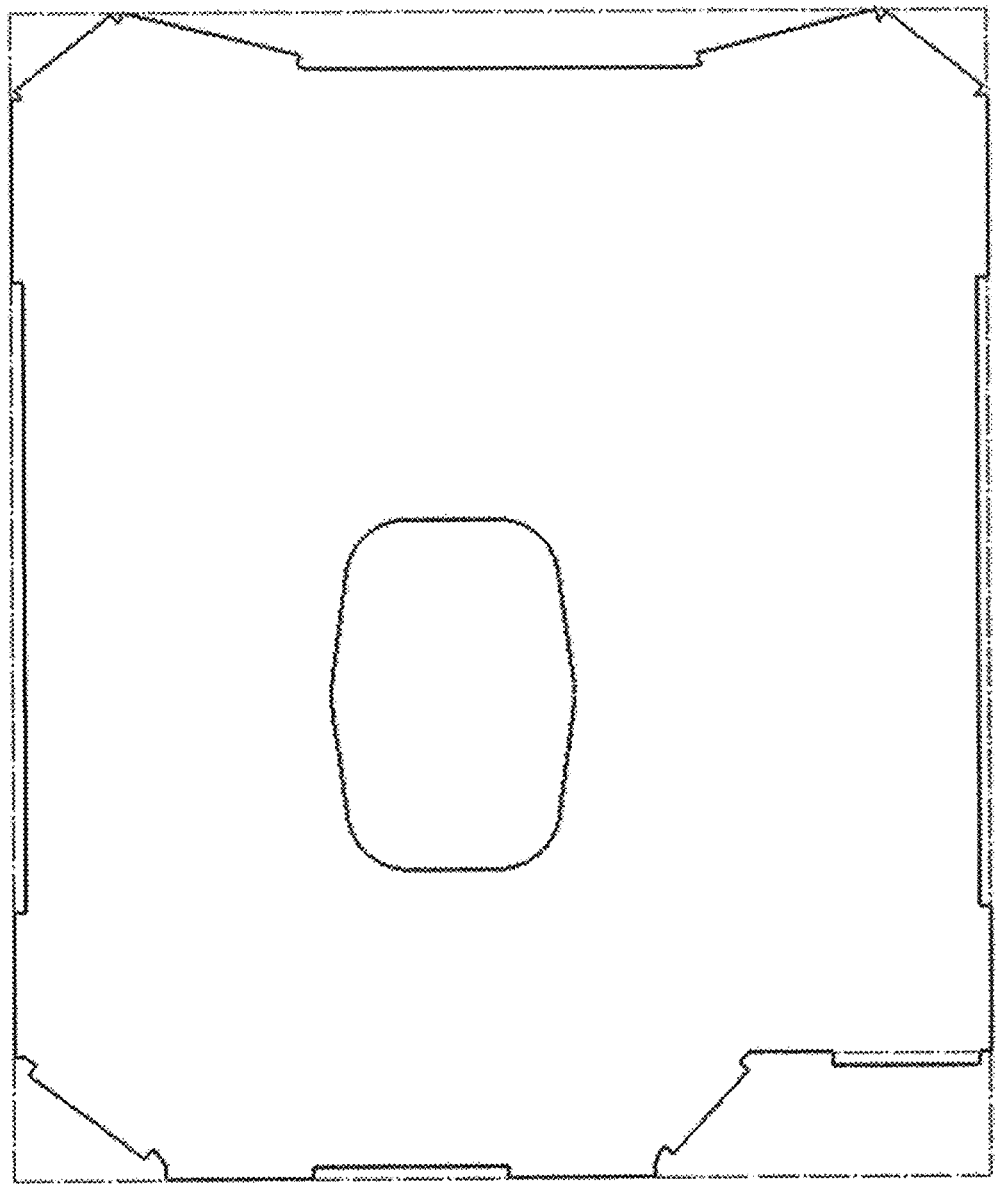
Figure 38:
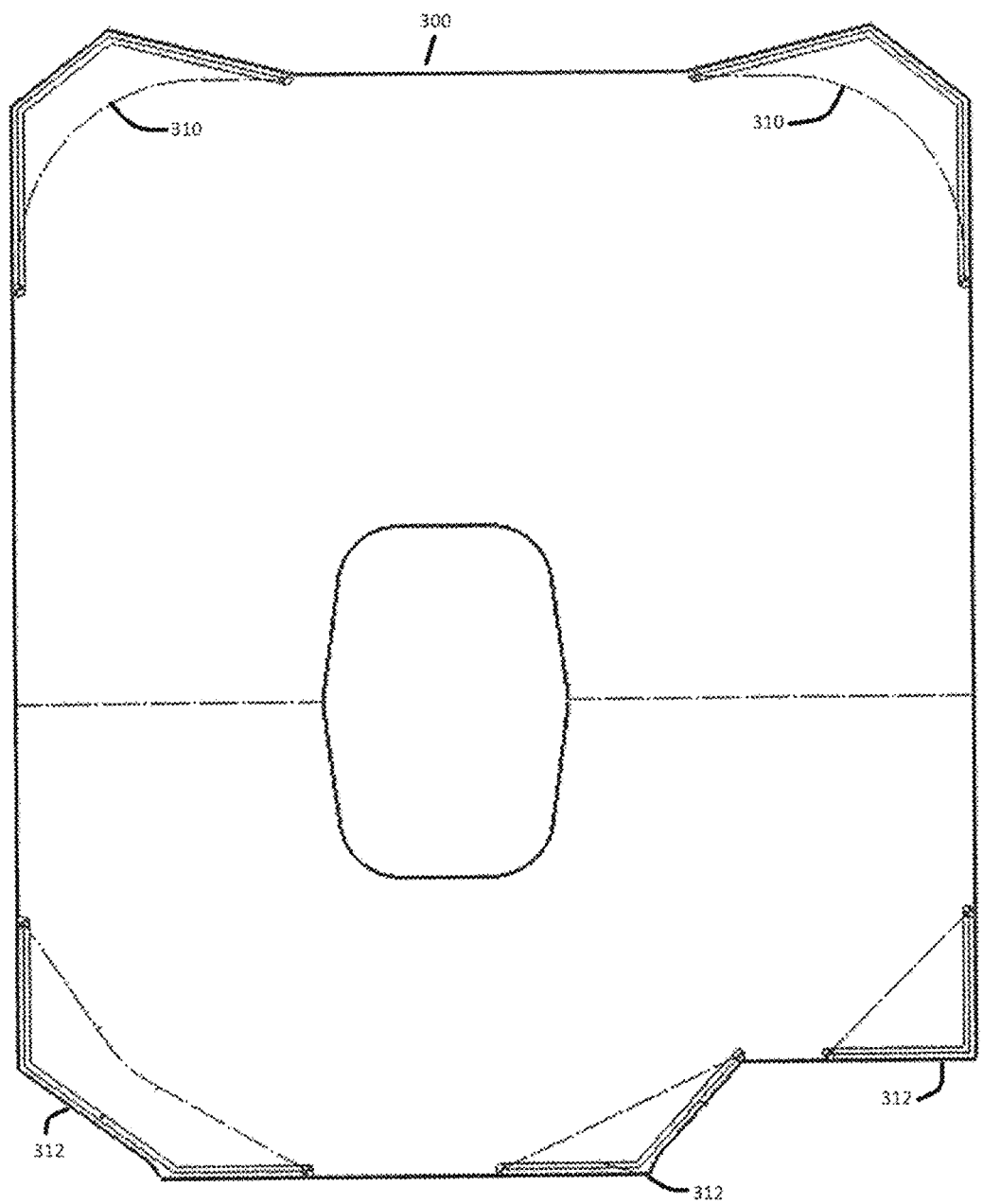
Figure 39:
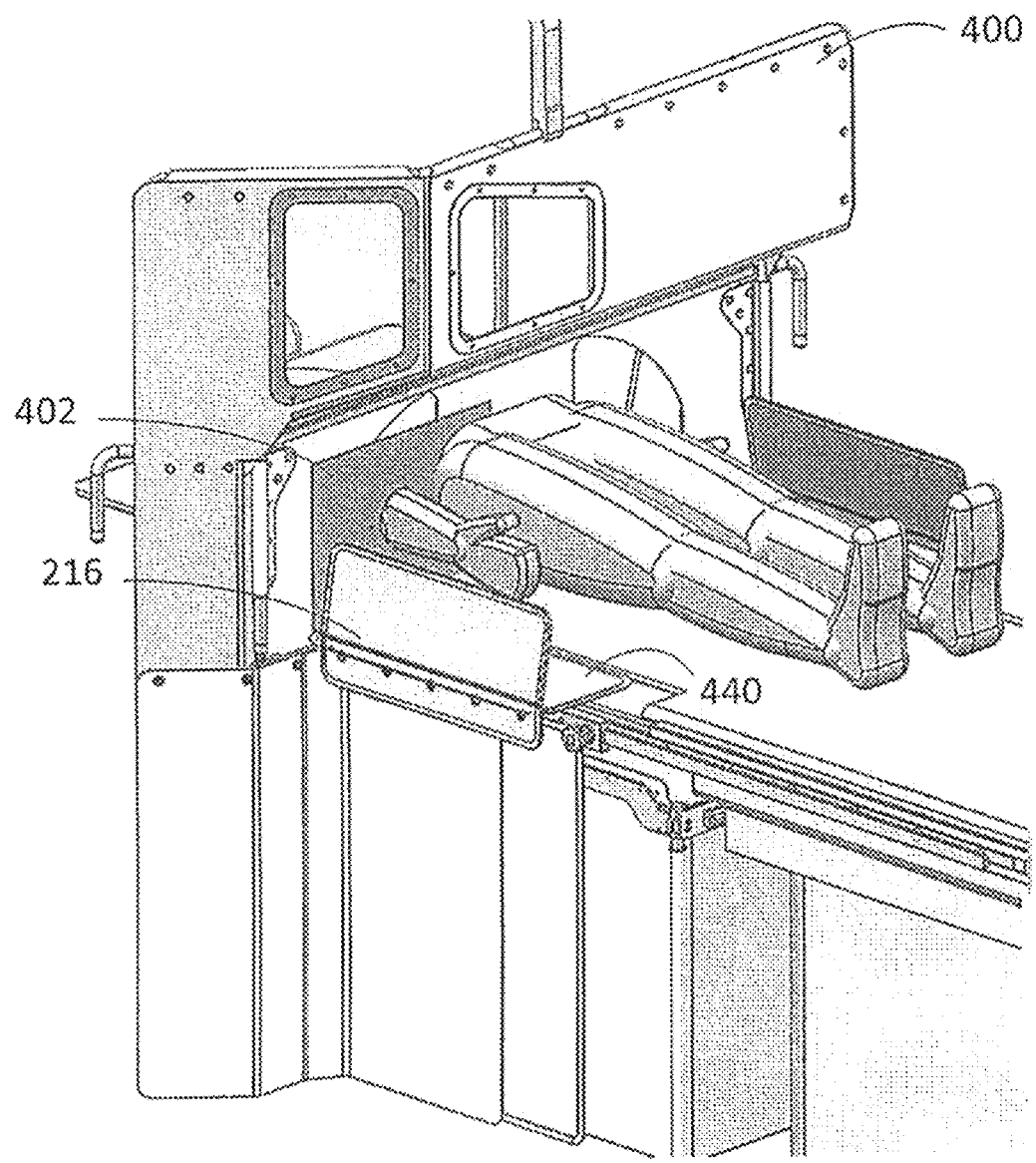
Figure 40:
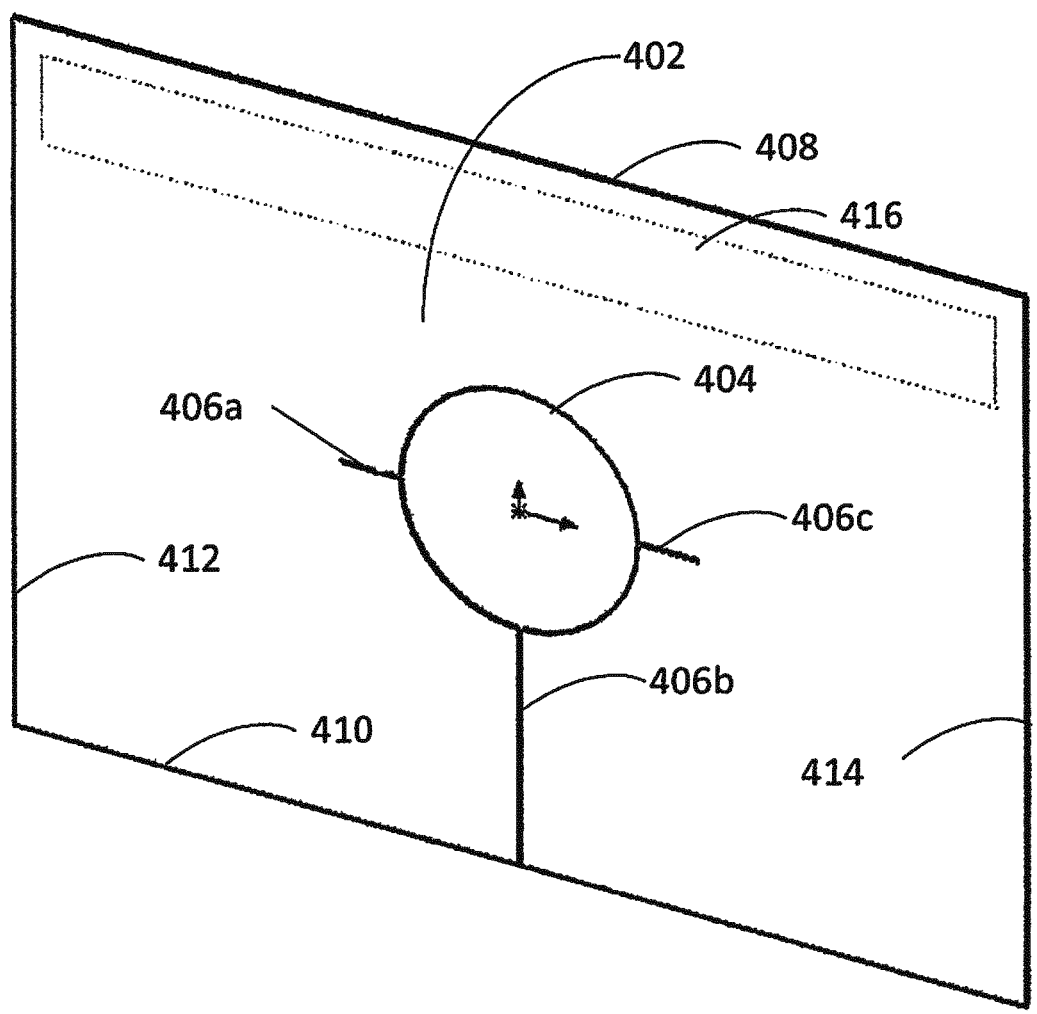
Figure 41:
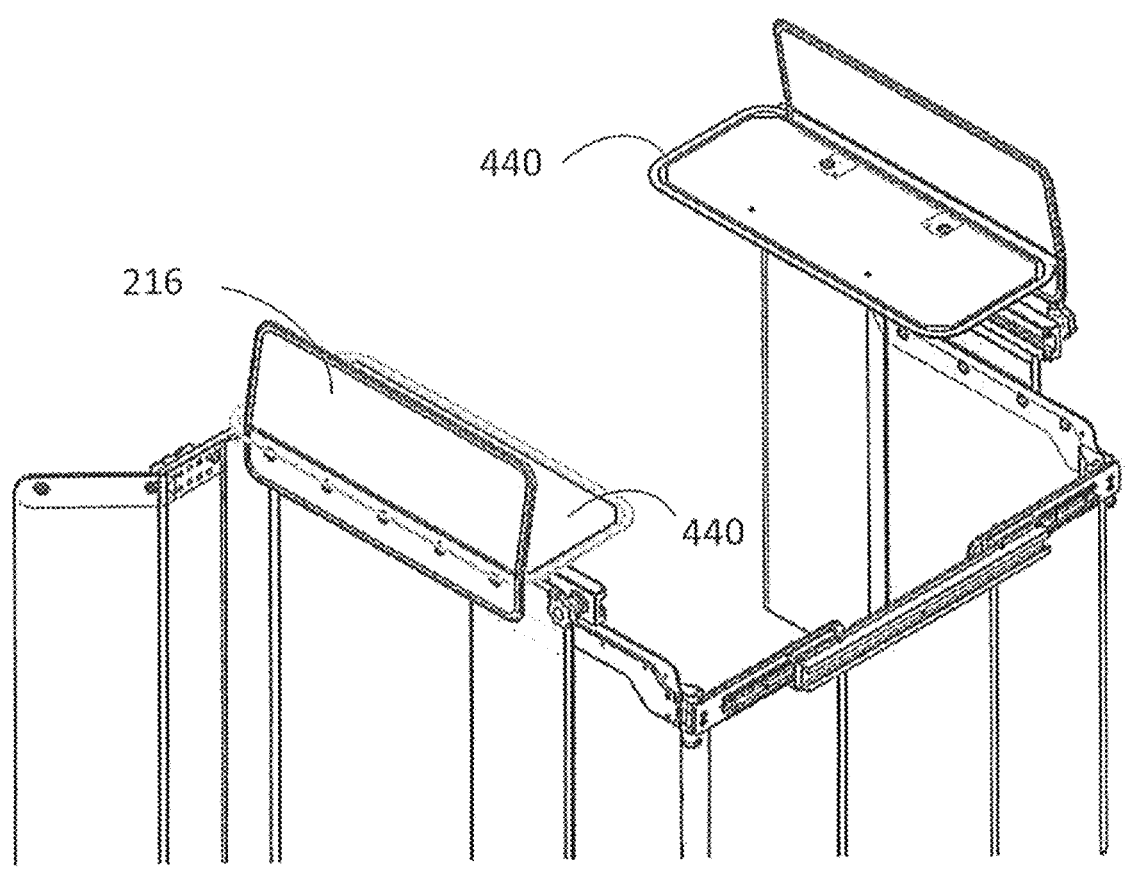
Figure 42:
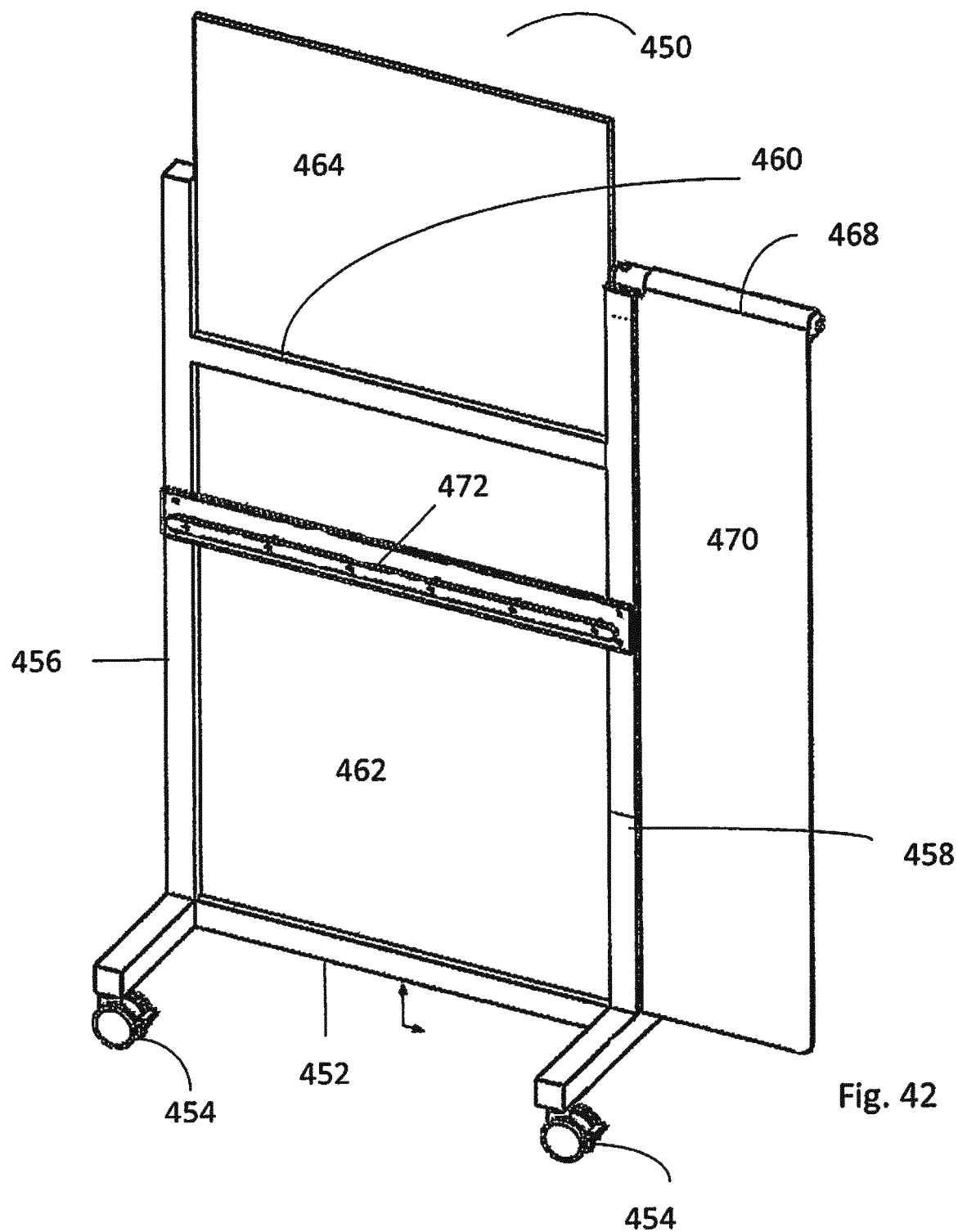
Figure 43:
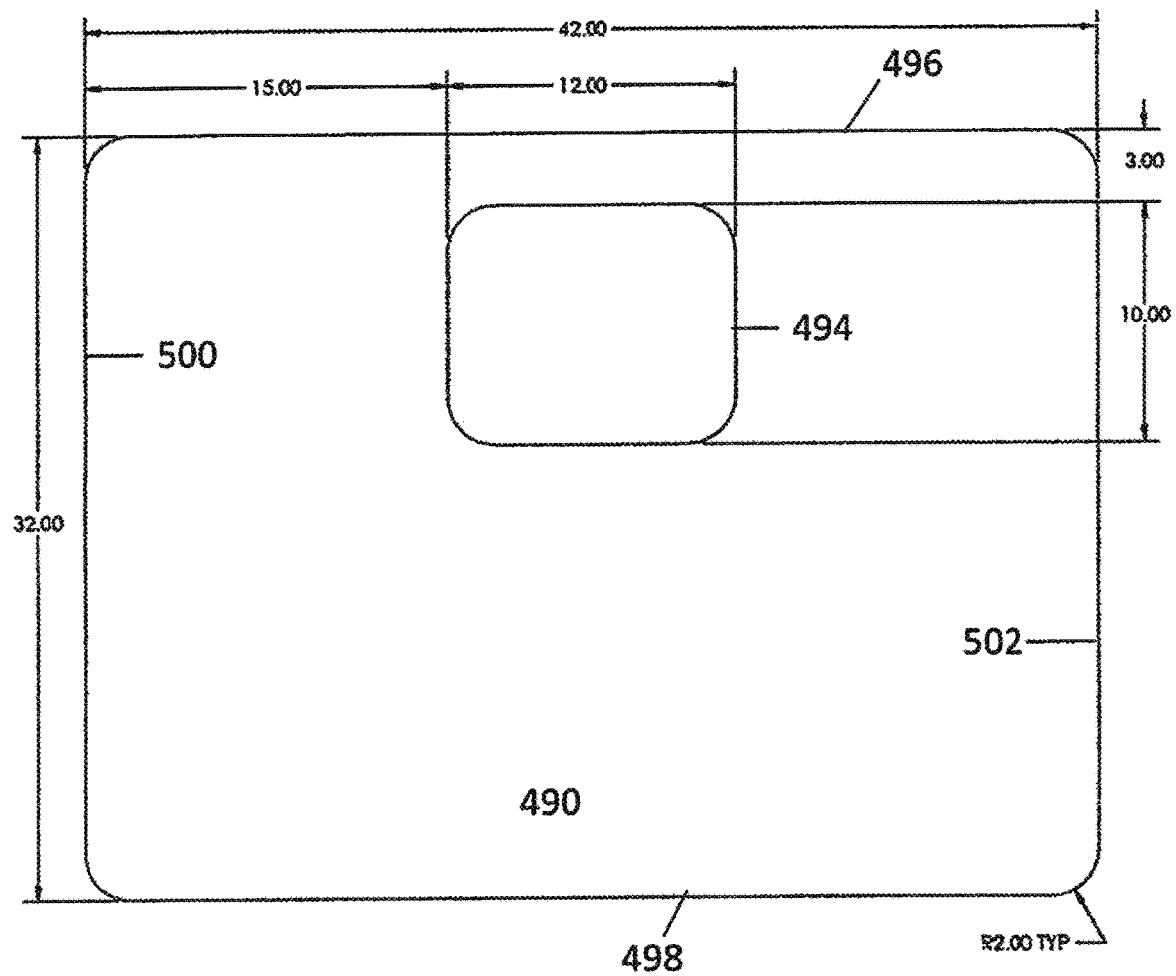

FIG. 28 is a perspective view of the lower shield assembly, showing the interior side of the shield assembly opposite the physician station FIG. 29 is an enlarged partial perspective view of the lower shield assembly as shown in FIG. 25, showing the mounting of the telescoping panels FIG. 30 is a perspective view of the lower base shield assembly, showing the interior side of the end of the shield assembly;

FIG. 31 is an enlarged partial perspective view of the lower base shield assembly as shown in FIG. 30, showing the mounting of the telescoping panels;

FIG. 32 is a perspective view of the lower base shield assembly, showing the exterior side of the end of the shield assembly;

FIG. 33 is an enlarged partial perspective view of the lower base shield assembly as shown in FIG. 25, showing the mounting of the telescoping panels;

FIG. 34 is a front perspective view of a disposable drape for the upper shield assembly;

FIG. 35 is a rear elevation view of the disposable drape;

FIG. 36 is a diagram showing the coverage of the disposable drape from the side;

FIG. 37 is a top plan view of a blank for fabricating the disposable drape;

FIG. 38 is a top unfolded plan view of the partially assembled disposable drape;

FIG. 39 is a front perspective view of an alternate embodiment of the shield;

FIG. 40 is a perspective view of an arm shield for blocking radiation around the subject's arm;

FIG. 41 is a perspective view of a waist shield panel adapted for use with the lower base shield of some embodiments of this invention;

FIG. 42 is a perspective view of a mobile barrier assembly useable with the shields of some of the embodiments of this invention;

FIG. 43 is a plan view of a leg shield for blocking radiation around the subject's leg.

Corresponding reference numerals indicate corresponding parts throughout the several views of the drawings.

DETAILED DESCRIPTION

Example embodiments will now be described more fully with reference to the accompanying drawings.

Figure 1:
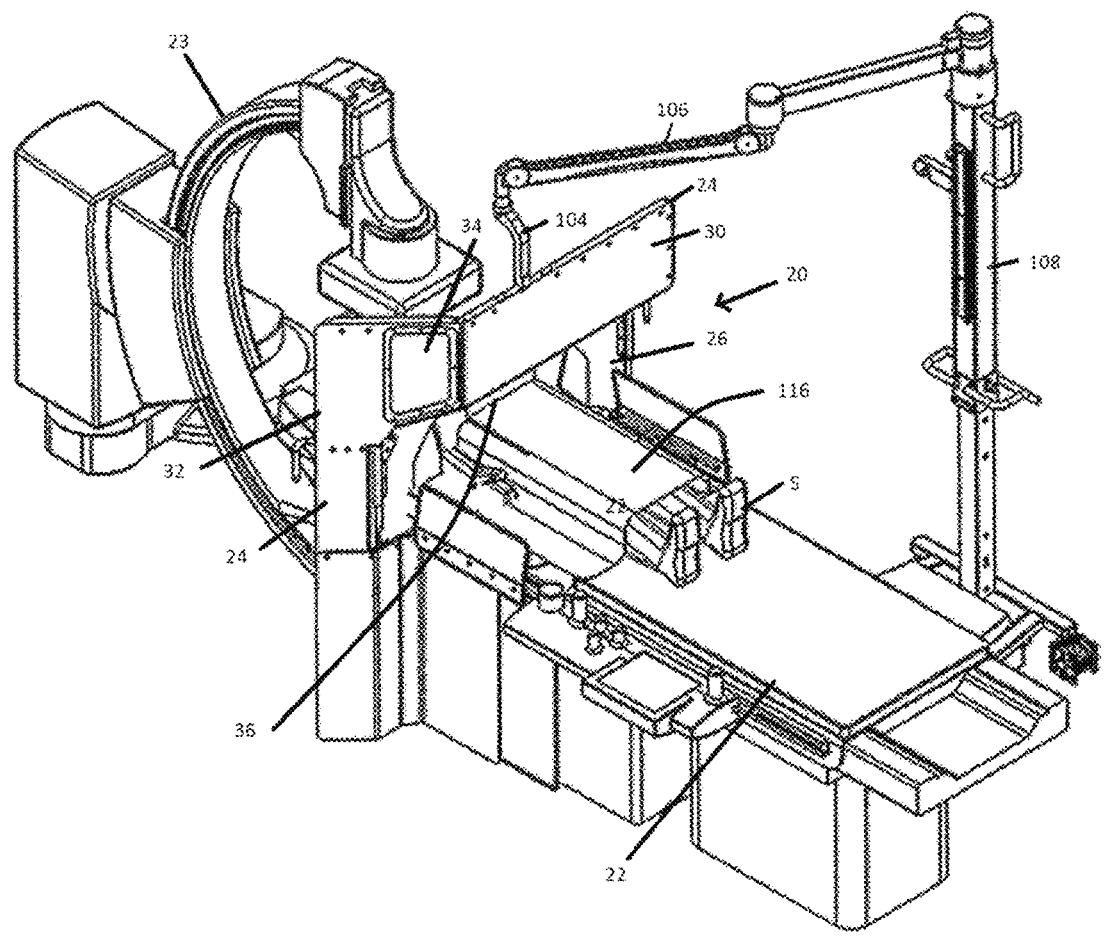
FIG. 1 is a front perspective view of an operating suite including an procedure table and C-arm imaging system in which a preferred embodiment of a shield according to the principles of this invention, is shown positioned over a subject on the procedure table.
Figure 2:
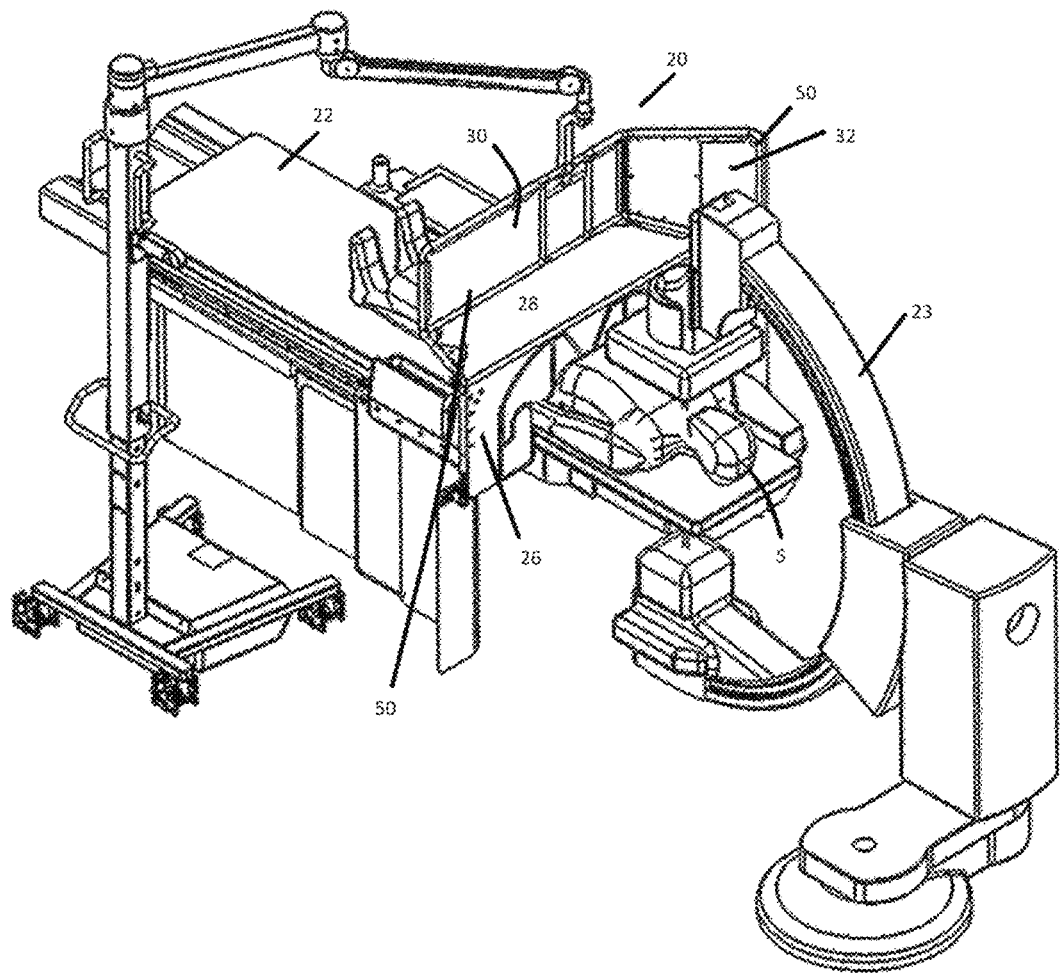
FIG. 2 is a rear perspective view of the operating suite with the preferred embodiment of the shield.

A preferred embodiment of a radiation shield in accordance with the principles of this invention, indicated generally as 20, is shown in FIGS. 1 and 2 as it would be used in an operating suite comprising an procedure table 22 and a C-arm mounting imaging system 23. As shown in FIGS. 1 and 2, the shield 20 is adapted to be disposed transversely across a subject S who is supported on the surface of the procedure table 22 to protect medical professionals working in front of the radiation shield from therapeutic or diagnostic radiation being applied to the subject behind the radiation shield, for example by the image system 23.

The radiation shield 20 preferably comprises an upper shield assembly and a lower shield assembly. The upper shield assembly preferably comprises a movable barrier 24 positionable transversely across the subject S supported on the surface of the procedure table 22. The barrier 24 preferably comprises a generally vertically-oriented lower section 26; a generally forwardly sloping intermediate section 28; and a generally vertically-oriented upper section 30, forwardly offset from the plane of the lower section. The barrier 24 also comprises a side section 32 that extends outwardly and rearwardly from one side of the lower, intermediate, and upper sections 26, 28 and 30.

One or more transparent radiopaque windows 34 can be provided in the side section 32 and/or the upper section 30, respectively. These windows 34 can be made of leaded acrylic/plastic which is shatter-resistant and has a lead equivalency of 0.3 mm to 0.5 mm.

There is a recess 36 in the lower edge 38 of the lower section 26 for accommodating a portion of the body of the subject S on the surface of the procedure table 22, with portions of the lower section on each side of the recess projecting downwardly below the surface of the procedure table. There are a plurality of flexible radiopaque overlapping flaps 40 comprising 94A, 94B, and 94C on the left side of the recess 36, and 96A, 96B, and 96C on the rights side of the recess. depending from the perimeter of the recess 36, for blocking radiation from penetrating the gap between the subject S and the perimeter of the recess 36. These flaps are preferably made of a flexible lead-free shielding with lead equivalence of 0.5 mm.

The barrier 24 is preferably formed from a skeleton or frame 50, with a plurality of radiopaque panels 52 mounted on the frame. These panels 52 may be rigid or flexible, and they are preferably releasably mounted to the frame 50. The frame 50 can be made of rods, or more preferably tubes.

Although the frame 50 can have many different configurations, as shown in FIGS. 5, 6, 10 and 11, in the preferred embodiment the frame comprises a left vertical section 54, a right vertical section 56. A resilient horizontal support 58 extends substantially across the barrier 24, and in the preferred embodiment is formed by double bungee strips, defining the top of the lower section 26, and the bottom of the intermediate section 28. On the left side, a member 60 extends forwardly, inwardly, and upwardly from the left vertical section 54. On the right side, a member 62 extends forwardly and upwardly from the right vertical section 56. A section 64 extends horizontally between the sections 60 and 62, forming the top of the sloped intermediate section 28, and the bottom of the upper section 30.

A vertical member 66 extends from the end of the member 60, and a vertical member 68 extends from the end of the member 62. A horizontal section 70 extends between the vertical members 66 and 68, forming the top of the upper section 30.

The upper section 30 is formed by three looped sections 72, 74, and 76. The looped section 72 is formed by part of the horizontal member 64, the vertical member 66, part of the horizontal member 70, and a vertical member 78. The looped section 74 is formed by part of the horizontal member 64, the vertical member 78, part of the horizontal member 70, and a vertical member 80. The looped section 76 is formed by part of the horizontal member 64, the vertical member 80, the horizontal member 70, and the vertical member 68.

The side section 32 comprises a horizontal member 82 extending rearwardly and outwardly from the vertical member 66, a vertical member 84 depending from the end of the horizontal member 82, a horizontal member 86 extending between the end of the vertical member 84 and the horizontal member 60.

In the preferred embodiment the plurality of panels 52 forming the barrier comprise a panel 88 mounted over loops 72, 74, and 76, to form the upper section 30. Panel 88 can have flaps that wrap around portions of the frame, and are secured, for example with snaps or hook-and-loop type fastening material. In some embodiments, panel 88 can extend downwardly and form part of the sloped intermediate section 28, and even part of the lower section 26. In other embodiments a separate panel is mounted over the frame to form the sloped intermediate section 28, and another panel can be mounted on the frame to form the lower section 26. There are a plurality of flaps 94A, 94B, and 94C on the left side of the recess 36, and a plurality of flaps 96A, 96B, and 96C on the left side of the recess, secured to the panel forming the lower section 26 to block radiation between the subject S, and the margins of the recess 36. The lower ends of the flaps 94B and 96B have recesses for accommodating the arms of the subject.

Handles 98 and 100 extend horizontally, and then vertically downwardly from the members 86 and 62, to facilitate manipulating the shield.

The height of the lower section of the barrier, and the slope of the intermediate panel are preferably such as to provide a vertical access space above a subject on the surface of the procedure table that is about 16 inches high and about 9 inches forward of the barrier 24. The intermediate section 28 preferably has a slope of about 65° (with respect to vertical). The side section 32 preferably forms an angle of about 45° (with respect to the axis of the procedure table and with the plane of the barrier). More preferably, the height of the lower section 26 of the barrier, and the slope of the intermediate section 28 are such that a cylinder of about 12 inches in diameter, whose axis is within about 10 (10¼) inches in front of the plane of the lower section, could fit between the subject and the barrier. The top of upper section 30 of the barrier 24 is at least about 36 inches above the surface of the procedure table 22. The side section 32 extends outwardly from the procedure table center 22 at least about 31 inches.

Figure 5:
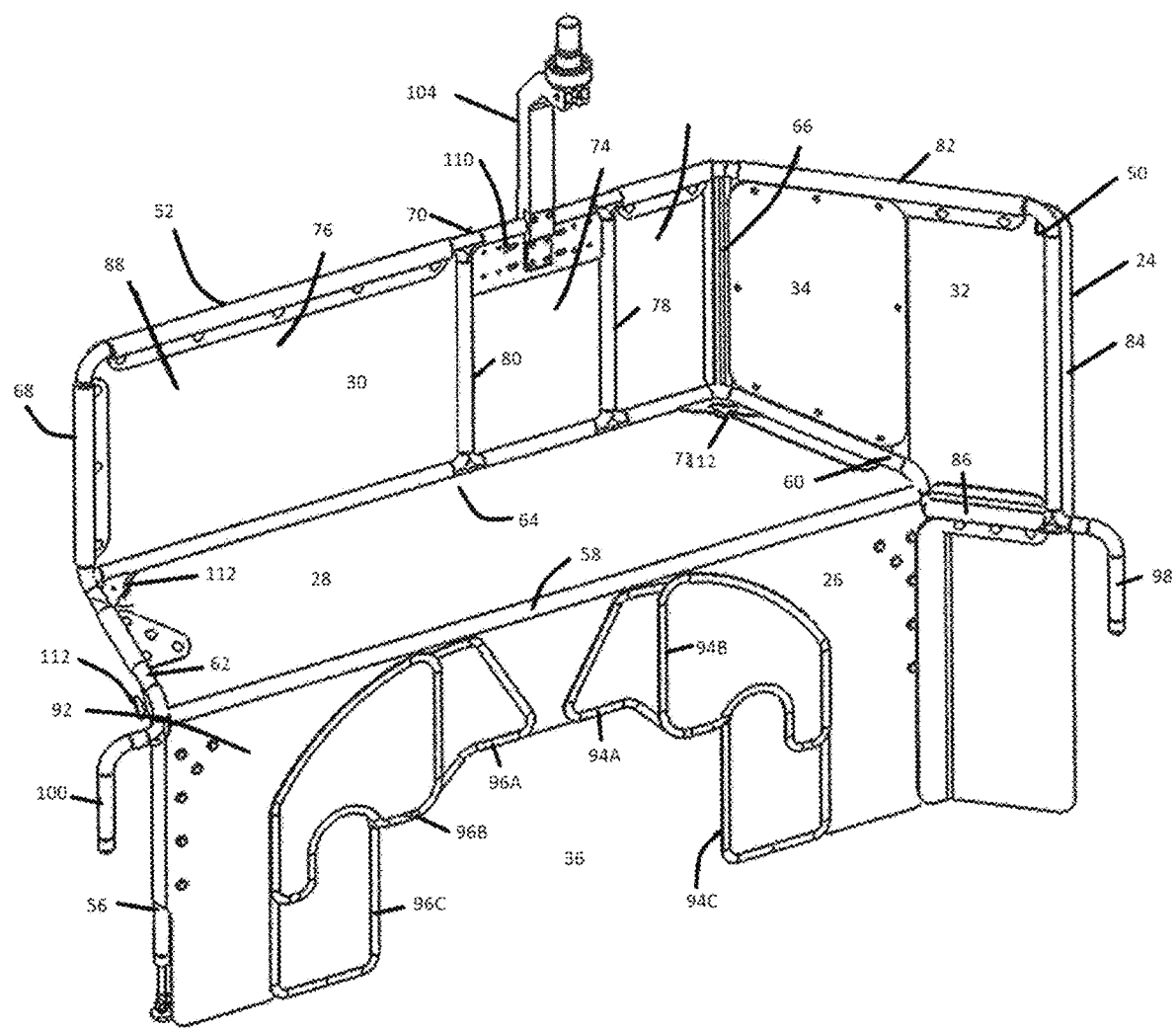
FIG. 5 is a rear perspective view of the preferred embodiment of the shield.
Figure 5A:
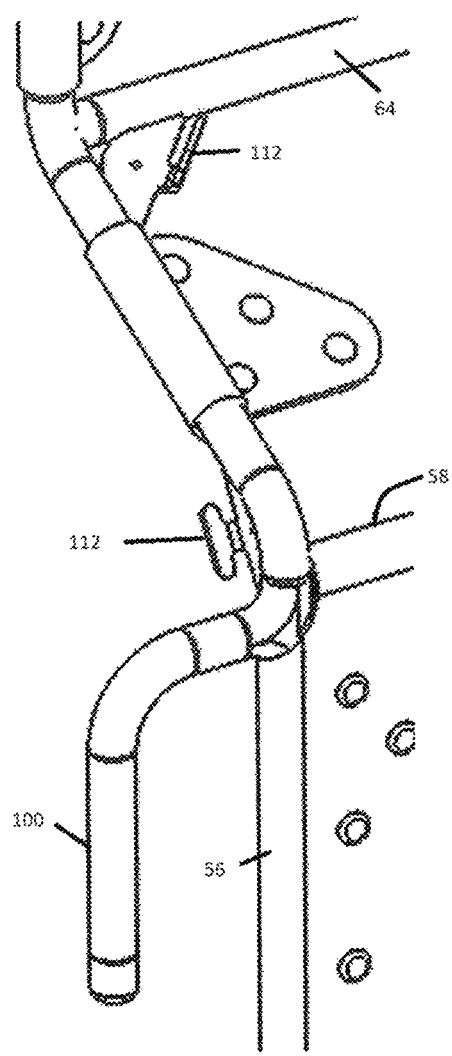
FIG. 5A is an enlarged partial perspective view of the handle on the left side of FIG. 5.
Figure 5B:
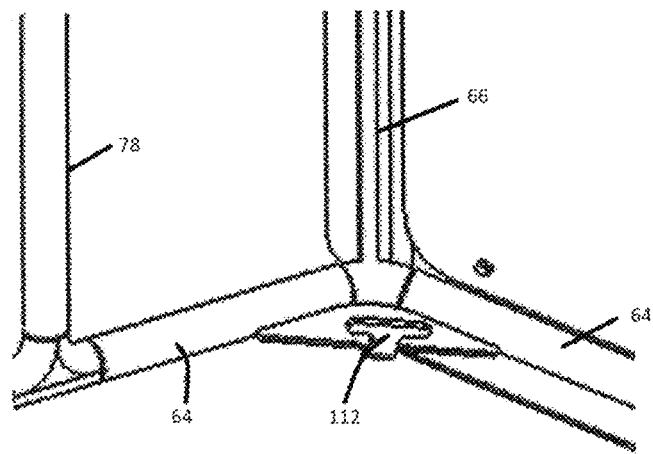
FIG. 5B is an enlarged partial perspective view of the inside corner on the right side of FIG. 5.
Figure 6:
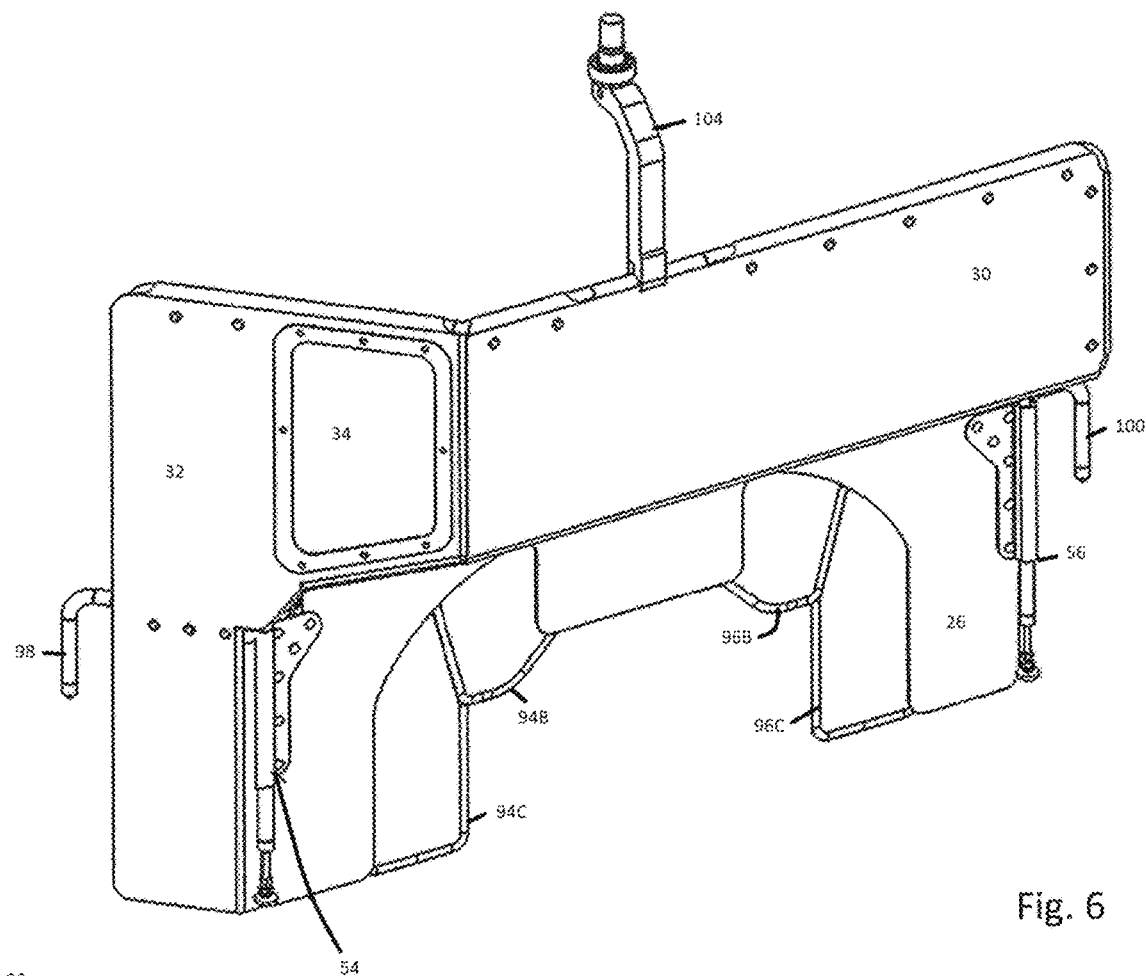
FIG. 6 is a front perspective view of the preferred embodiment of the shield.

As shown in FIGS. 1 and 2, the barrier 24 preferably has a bracket 104 adapted to be mounted on an articulated arm 106 extending from a stationary or moveable post 108, or from a ceiling mount (not shown). The upper end of the bracket 104 is preferably rotatably mounted to the articulated arm or ceiling mount, so that the barrier 24 can rotate about a vertical axis to accommodate movement of the C-arm of the imaging system. The upper end of the bracket 104 is preferably also hinged so that the barrier 24 can pivot, preferably at least about 5°, and more preferably about 10° about a generally horizontal axis to accommodate movement of the C-arm. As shown in FIG. 5, the lower end of the bracket 104 can be attached to the shield with a plate 110 that is secured to the frame.

A plurality of cleat hooks 112 are disposed on the frame for securing a disposable drape, described below.

As shown in FIGS. 1 and 2, and in more detail in FIGS. 19-34 Additional shielding, in the form of a lower shield assembly can be provided to protect the lower portions of the health care professionals' bodies. For example the shielding could be hung on the rail system of the procedure table 22. The shielding could be secured with mechanical or magnetic fasteners.

Figure 19:
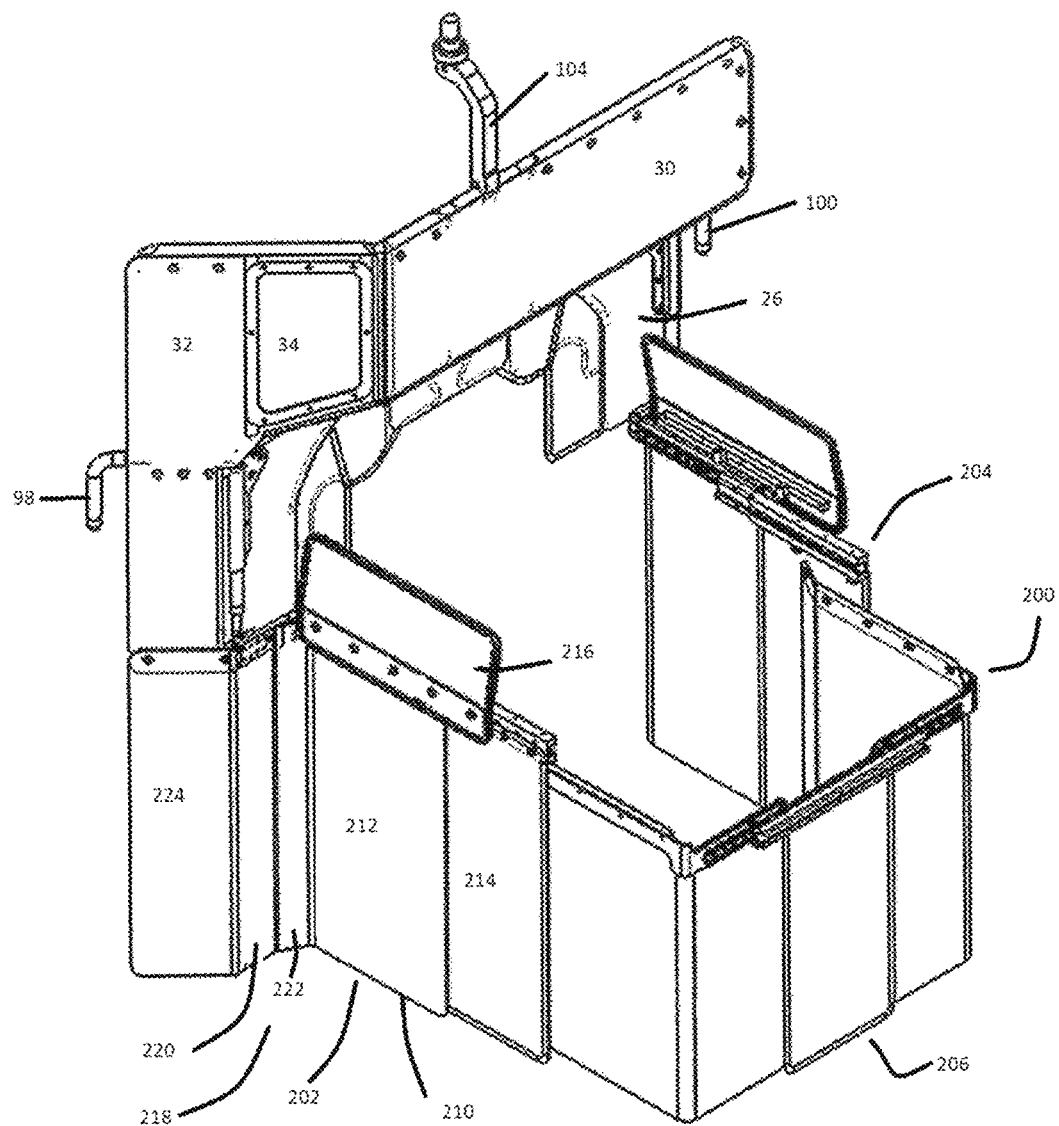
FIG. 19 is a perspective view of the upper and lower shield assemblies.
Figure 20:
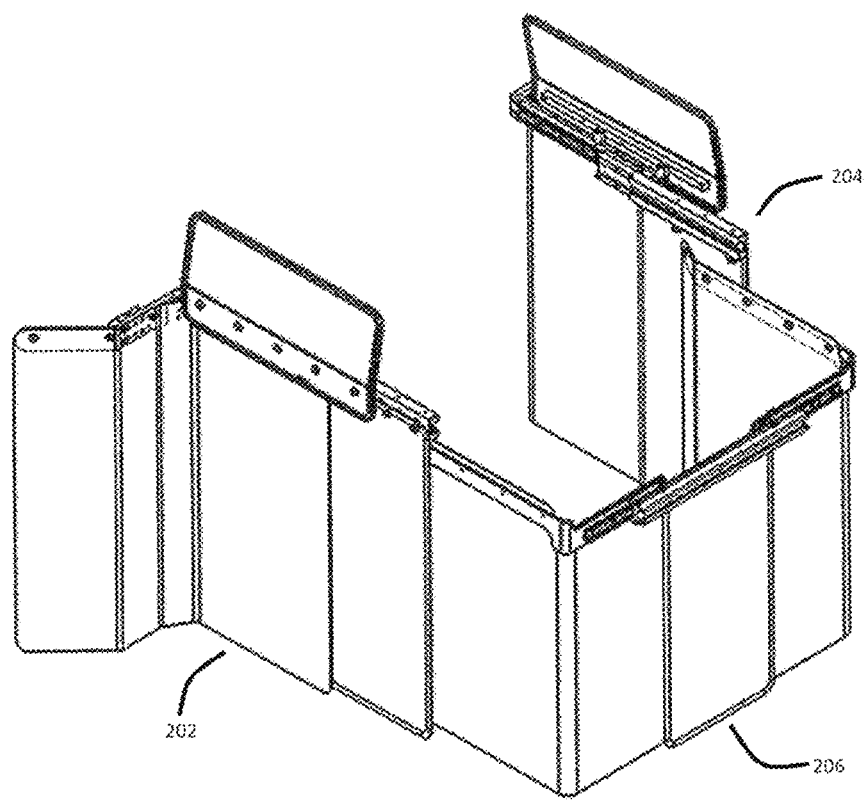
FIG. 20 is a perspective view of the lower shield assembly.
Figure 21:
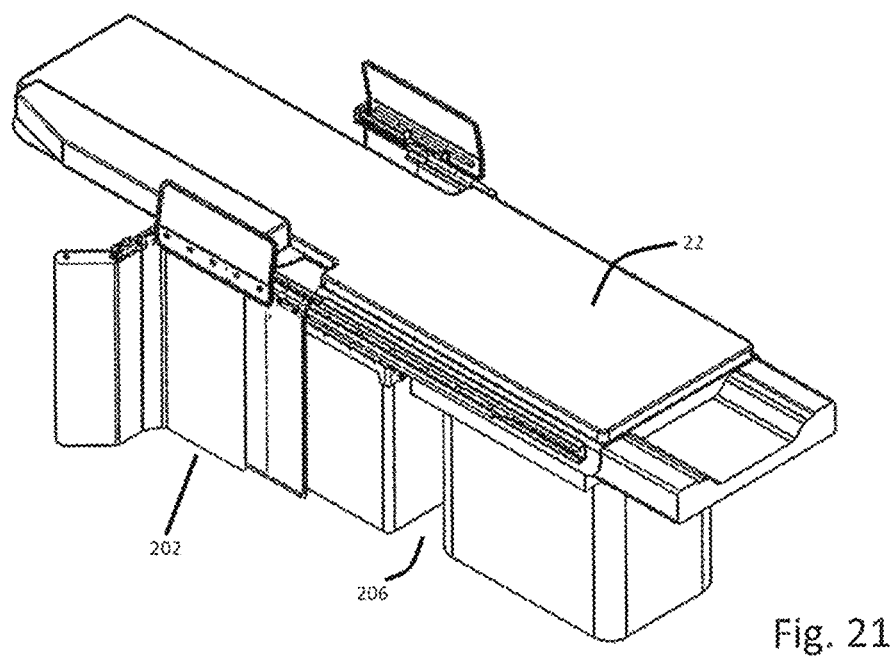
FIG. 21 is a perspective view of the lower shield assembly as it would be installed around a patient bed.
Figures 22, 23:
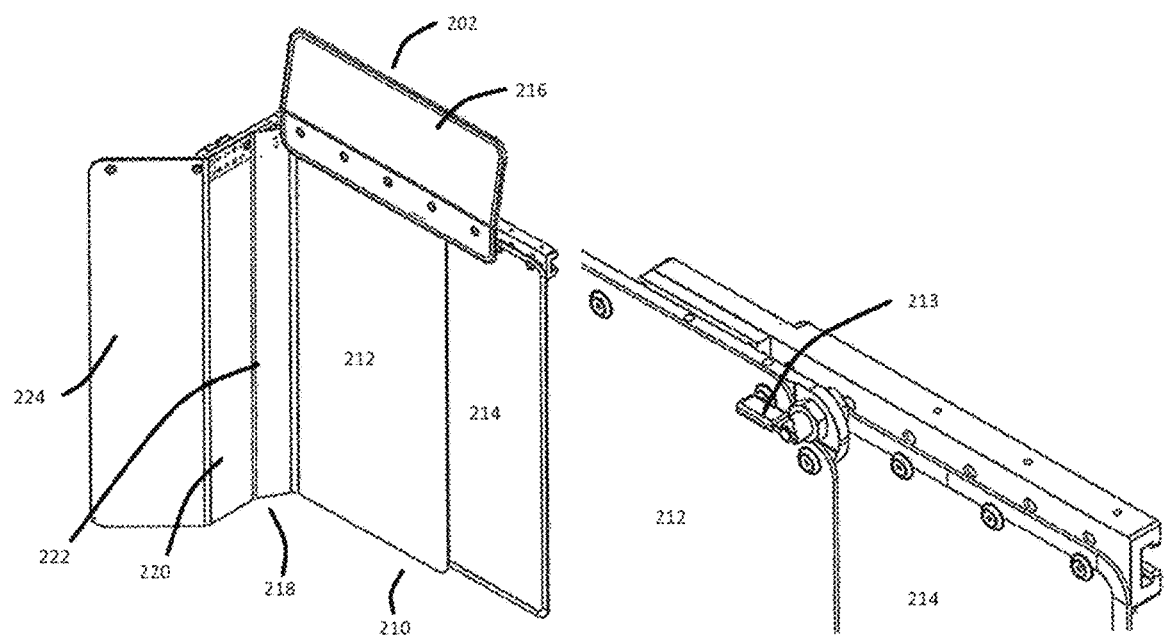
FIG. 22 is a perspective view of the lower shield assembly, showing the exterior side of the shield assembly adjacent the physician station.
FIG. 23 is an enlarged partial perspective view of the lower shield assembly as shown in FIG. 22, showing the mounting of the telescoping panels.

A preferred embodiment of the lower assembly of the shielding is indicated generally as 200 in FIGS. 19-21. The lower assembly 200 comprises a left side station shield 202, a right side station shield 204, and an end shield 206. The lower assembly is preferable configured and constructed of materials that provide equivalent shielding of 0.5 mm of lead.

As shown in FIGS. 22-25, the left side station shield 202 comprises a telescoping section 210 comprising first and second telescoping panels 212 and 214, which can move relative to each other to accommodate different table base lengths. A lock 213 can be provided to secure panels 212 and 214 in their desired relationship. A sloped belly shield panel 216 is preferably mounted on the telescoping section 210. The belly panel 232 is preferably made of a radiation shielding rated at 0.3-0.5 mm.

The left side station shield, 202 further comprises a telescoping section 218, extending generally perpendicularly outwardly from the left edge of telescoping section 210. The telescoping section 218 comprises first and second telescoping panels 220 and 222, can move relative to each other to accommodate different table widths. A panel 224 extends outwardly from the left edge of telescoping section 218, at an angle to align with the sloped side section 32.

The left side station shield 202 can be secured to the rails of the patient support 22, for example via magnets. A magnetic switch 202A can be provided to magnetically lock and magnetically release the left side station shield from the patient support 22.

As shown in FIGS. 26-29, the right side station shield 204 comprises a telescoping section 226 comprising first and second telescoping panels 228 and 230, which can move relative to each other to accommodate different table base lengths. A lock 229 can be provided to secure panels 228 and 230 in their desired relationship A sloped belly shield panel 232 is preferably mounted on the telescoping section 226. The belly panel 232 is preferably made of a radiation shielding rated 0.3-0.5 mm.

The right side station shield 204 further comprises a telescoping section 234, extending generally perpendicularly outwardly from the right edge of telescoping section 226. The telescoping section 234 comprises first and second telescoping panels 236 and 238, can move relative to each other to accommodate different table widths.

The right side station shield 204 can be secured to the rails of the patient support 22, for example via magnets. A magnetic switch 204A can be provided to magnetically lock and magnetically release the right side station shield from the patient support 22.

As shown in FIGS. 30-33, the end shield 206 comprises a telescoping center section 240, having a fixed shield section 242 and first and second telescoping panels 244, and 246, which can move relative to each other to accommodate different table base widths. The inventors have found that a width of between about 24 inches and about 32.5 inches is sufficient to accommodate most subject supports 22. A left side panel 248 extends generally perpendicularly rearwardly from the left side of the panel 244, and has an outwardly flaring lip 250 to engage with the left station shield 202. Similarly, a right side panel 252 extends generally perpendicularly rearwardly from the right side of the panel 246, and has an outwardly flaring lip 254 to engage with the right station shield 202.

Figure 3:
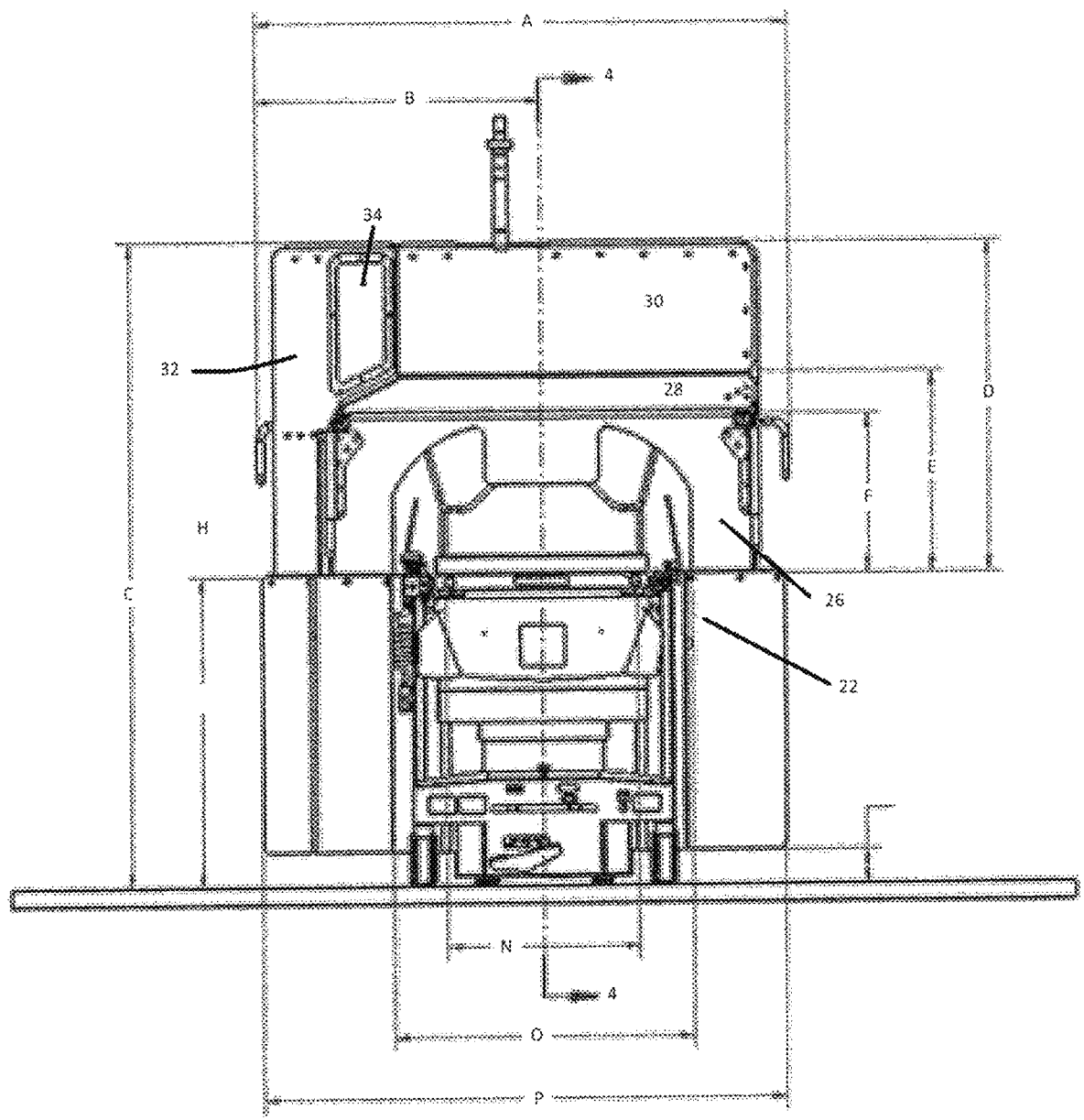
FIG. 3 is a front elevation view of the preferred embodiment of the shield, shown as it would be positioned over the procedure table.
Figure 4:
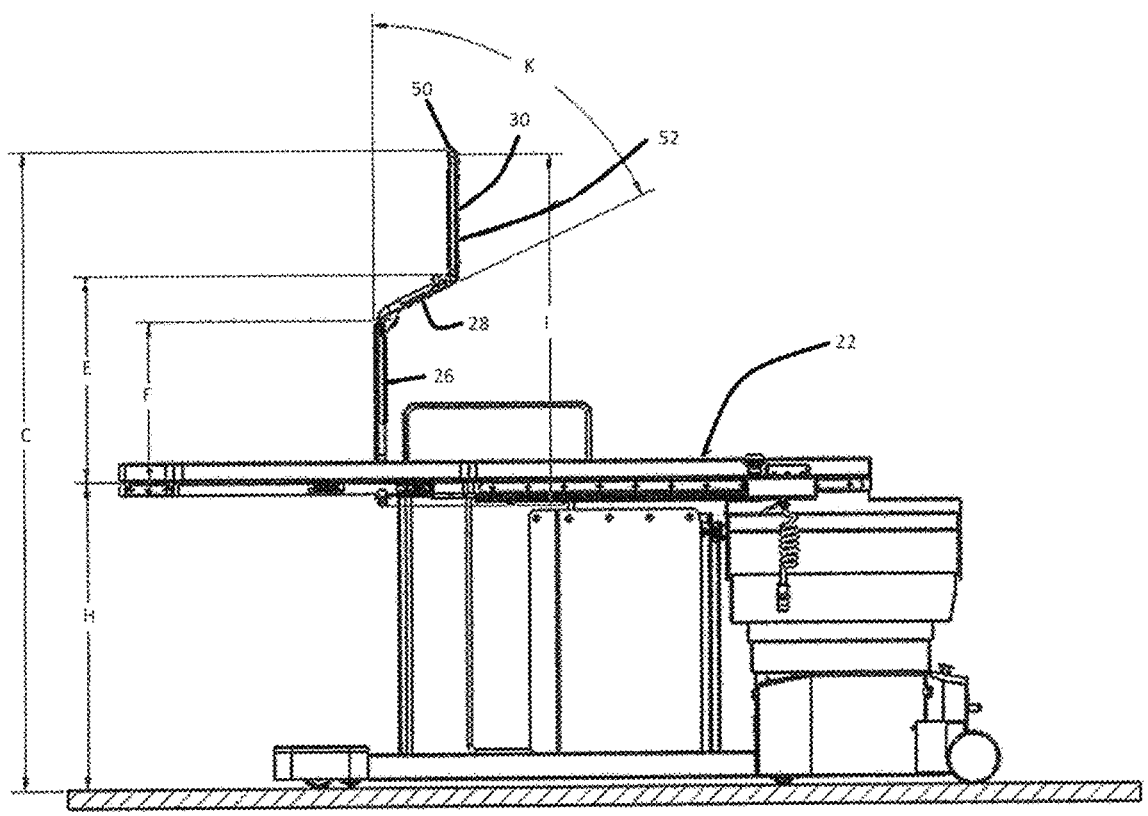
FIG. 4 is a longitudinal cross-sectional view of the preferred embodiment of the shield and procedure table, taken along the plane of line 4-4 in FIG. 3.
Figure 7:
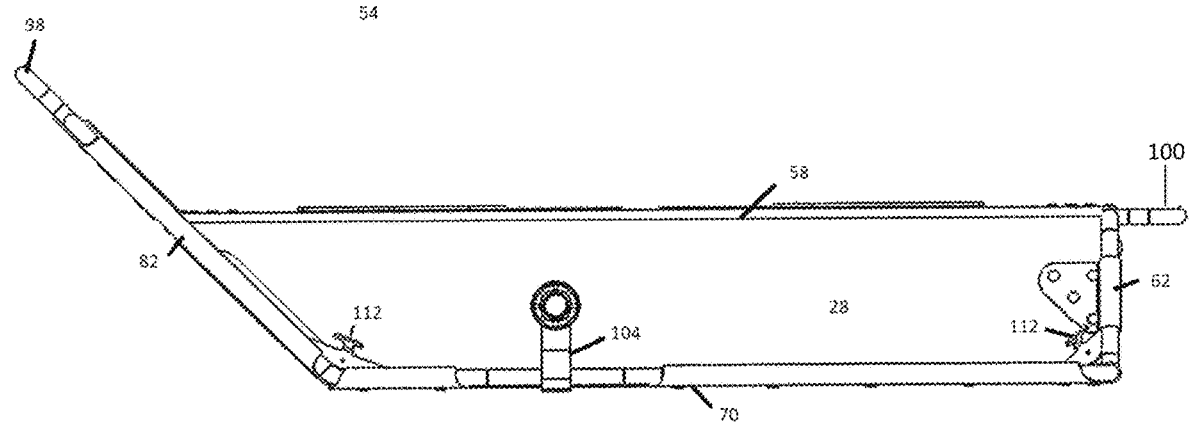
FIG. 7 is a top plan view of the preferred embodiment of the shield.
Figure 6A:
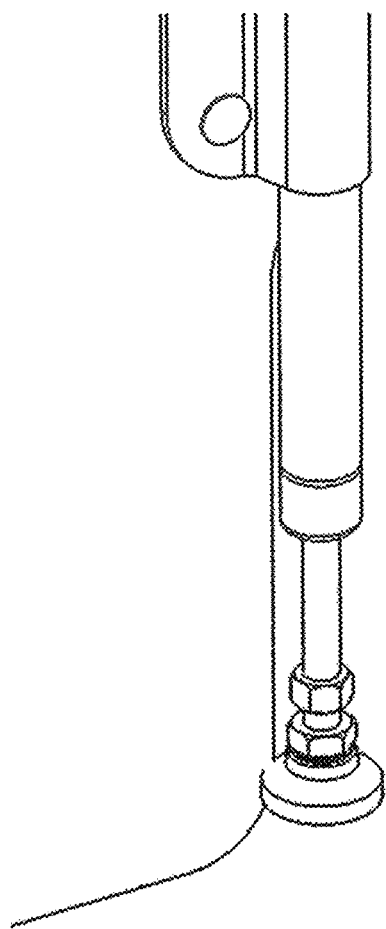
FIG. 6A is an enlarged perspective view of the table rail extension stabilizer on the right side of FIG. 6.
Figures 8, 8A:
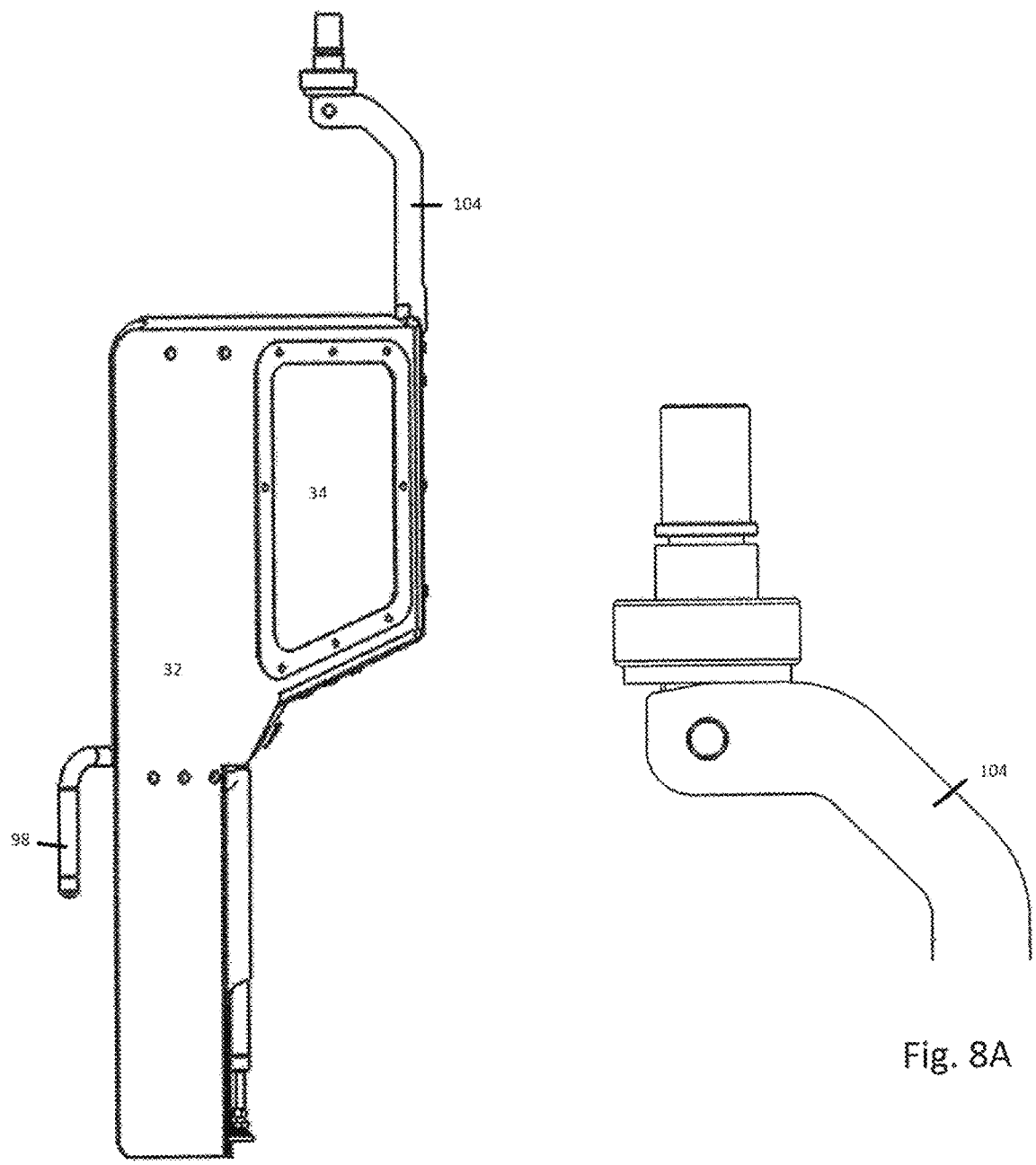
FIG. 8 is a right side elevation view of the preferred embodiment of the shield.
FIG. 8A is an enlarged side elevation view of the suspension mount at the top of FIG. 8.
Figure 9:
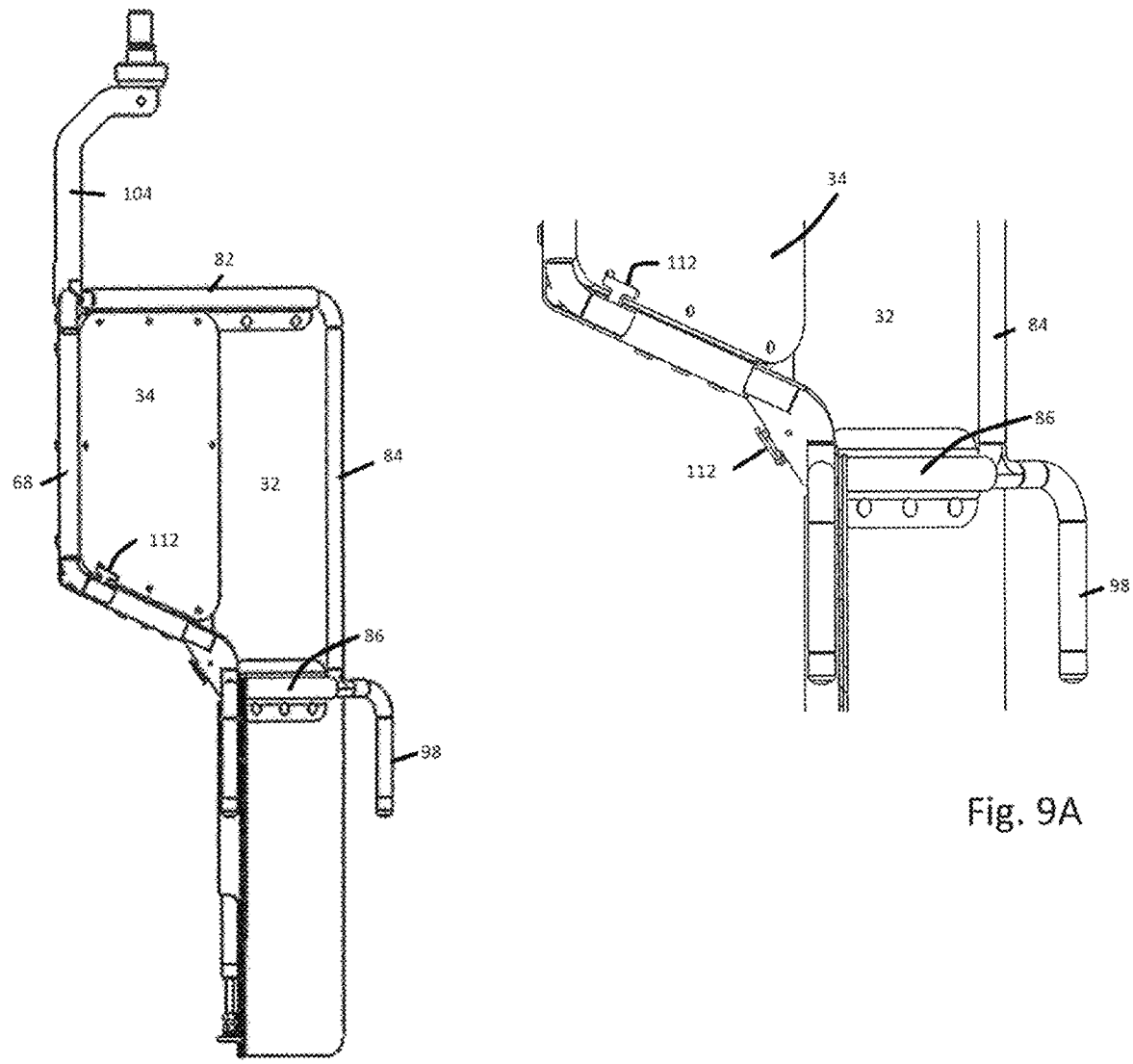
FIG. 9 is a left side elevation view of the preferred embodiment of the shield.
Figure 11:
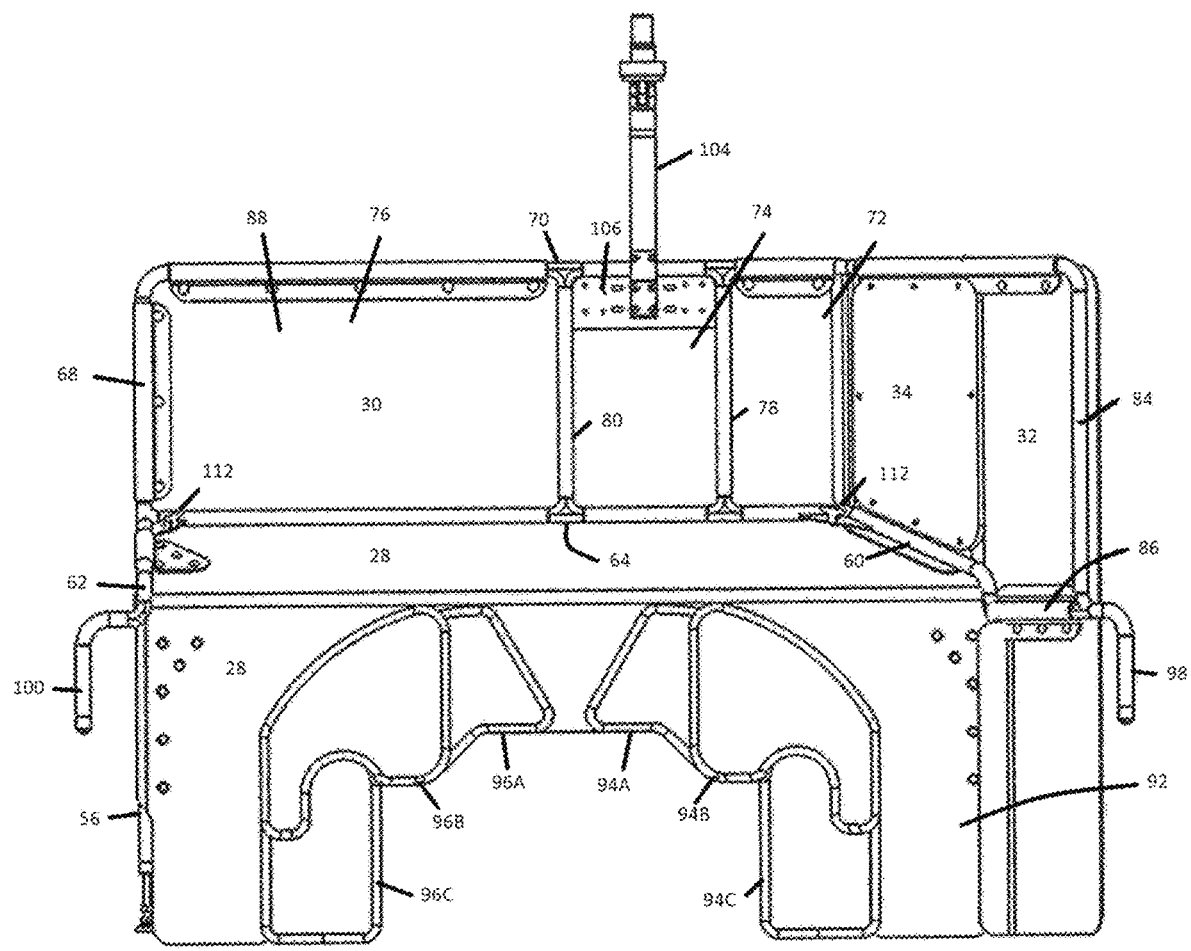
FIG. 11 is a rear elevation view of the preferred embodiment of the shield.
Figure 12:
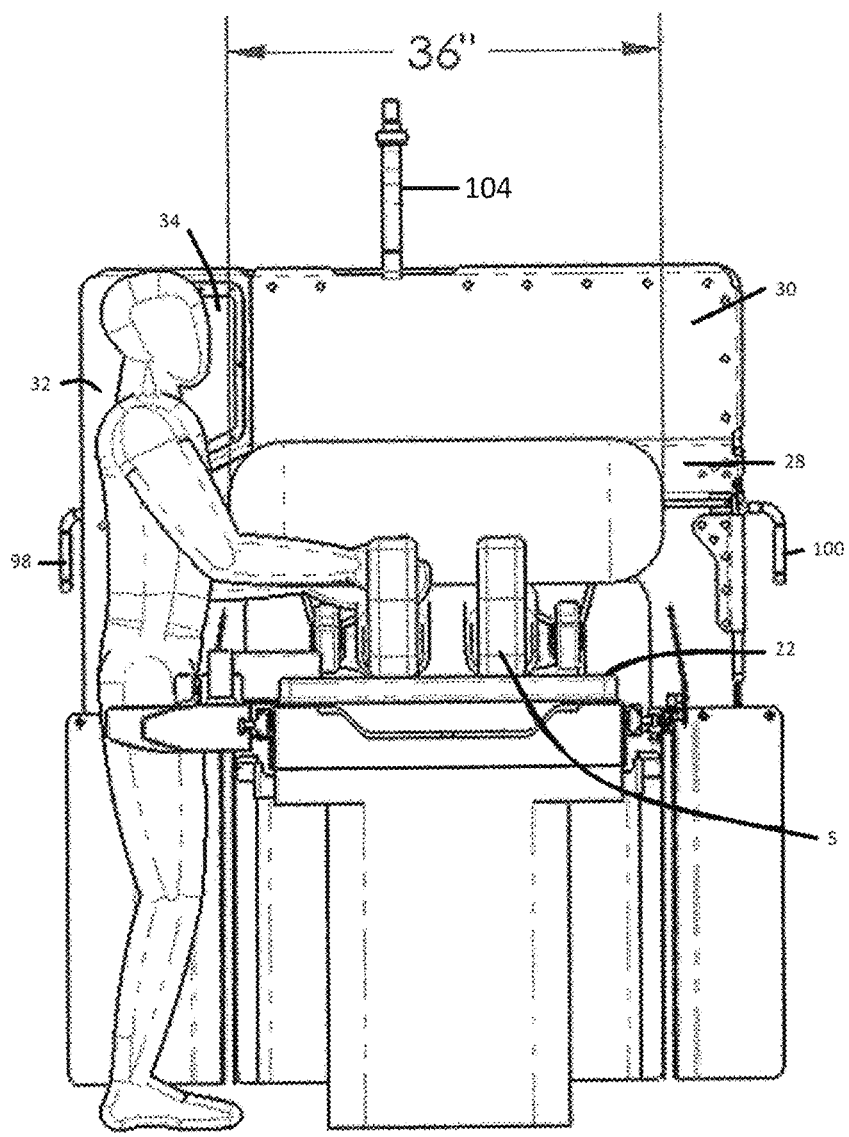
FIG. 12 is a front elevation view of the system showing a physician or other health care worker positioned in front of the shield with patient.
Figure 13:
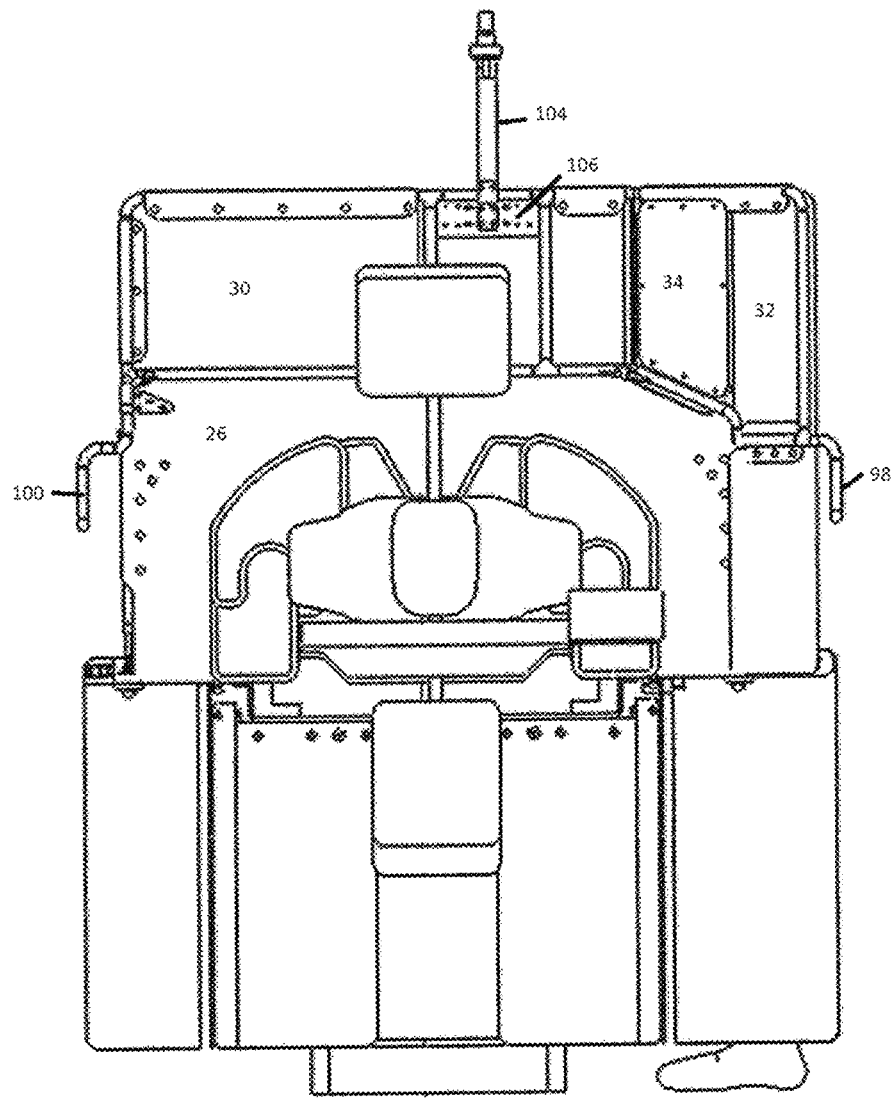
FIG. 13 is a rear elevation view of the system showing a patient positioned on the table with shield system in place.

Although the dimensions of a shield constructed according to the principles of this invention can vary, the shield of the preferred embodiment has the followings, reference being had to FIGS. 3, 4 and 7:

| Reference | Description | Value |
|---|---|---|
| A | Width of barrier | 60 |
| B | Distance from side section to center line | 32 |
| C | Height of barrier from floor | 72 |
| D | Height of the top of the barrier from centerline of procedure table | 37 |
| E | Height of the top of the intermediate section from centerline of procedure table | 23 |
| F | Height of lower section from the centerline of procedure table | 18 |
| H | Height of centerline of procedure table | 35 |
| I | Total height of barrier | 39.5 |
| K | Slope of intermediate Section | 65° |
| L | Depth of barrier | 16.25 |
| M | Angle of side section | 45° |
| N | Width of inside of the opening | 22 |
| O | Width of the outside of the opening | 34 |
| P | Width of the lower assembly | 59 |

Operation

In operation, the barrier 24 is covered with one or more sterile drapes. With the subject S positioned on the procedure table 22, the shield 20 is used by positioning the barrier 24 transversely across the subject, with the subject extending through the recess 36 in the lower edge 38 of the lower section 26 of the barrier, and separating the operating space into a physician space in front of the shield, and an operating field behind the shield. The configuration of the barrier 24, and in particular the size and orientation of the lower, intermediate, and upper sections 26, 28, and 30 of the barrier, allows conventional C-arm mounted imaging equipment 23 full imaging access to the portion of the subject S in which the procedure is being conducted.

Typically the physician is accessing the operating region in the subject via blood vessels in the arms and legs, which extend through the barrier 24 to the front. The flaps 94A-C and 96A-C help block the gaps between the recess 36 and the subject S. Additional radiopaque draping 116 on the subject S overlapped by the flaps 94A-C and 96A-C provides further protection against radiation transmitted through the subject S. The draping 116 can have a window closable with a flap to give the medical professional to the subject's vasculature.

Figure 14:
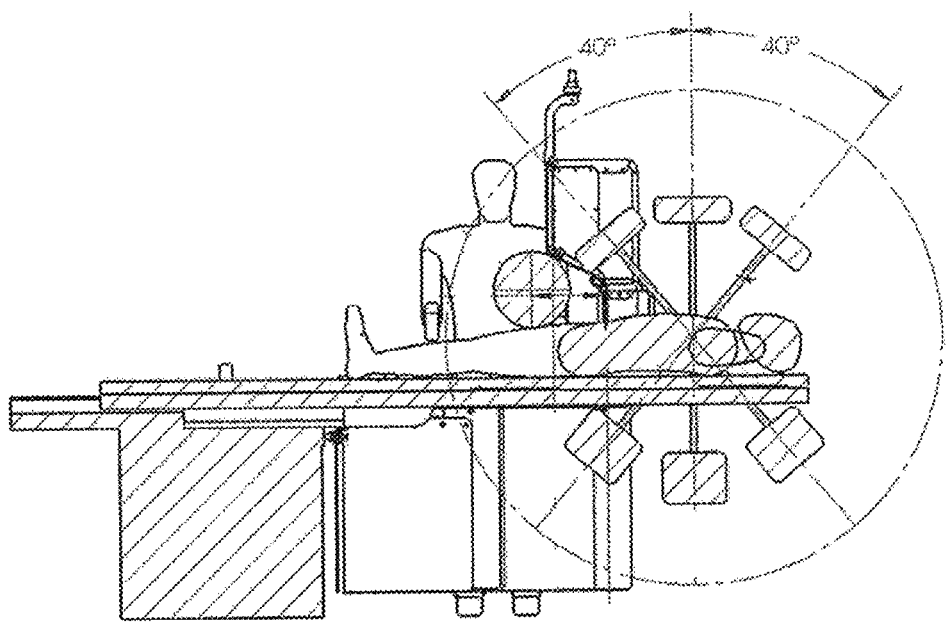
FIG. 14 is a longitudinal cross sectional view of the system, taken along the plane of line 14-14 in FIG. 13, showing how the shield accommodates motion of the C-arm mounted imaging system.
Figure 15:
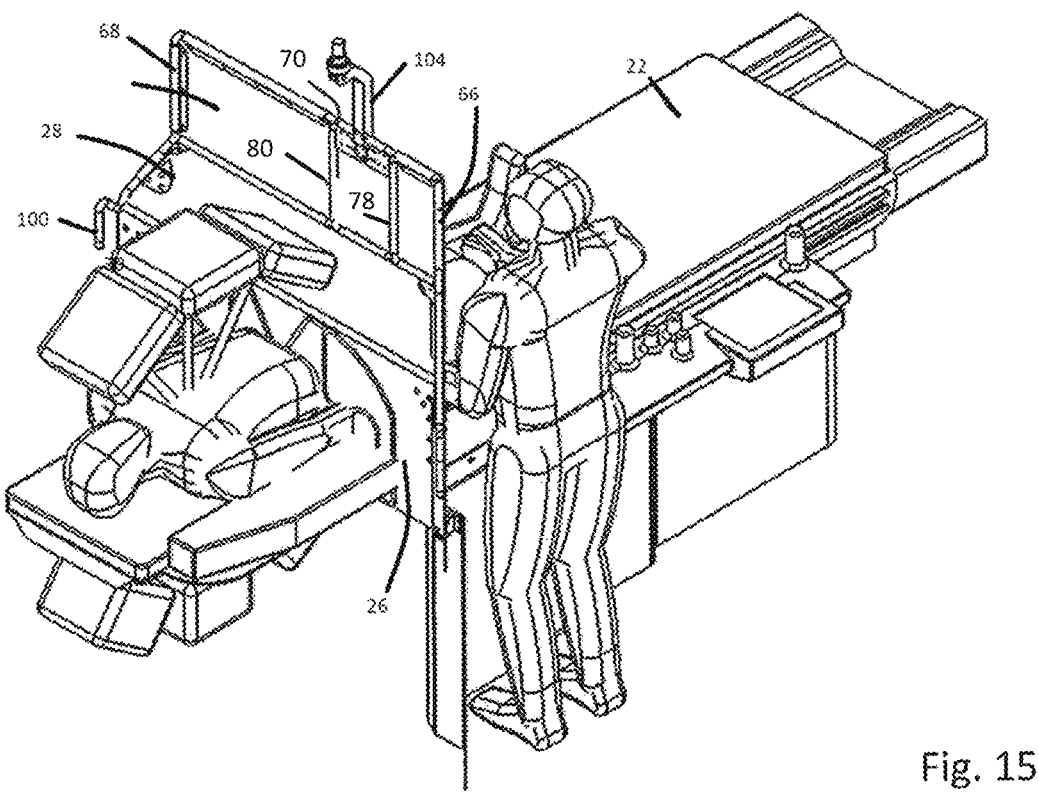
FIG. 15 is a rear perspective view of the system, showing a physician or other health care worker positioned in front of the shield, showing how the shield accommodates motion of the C-arm mounted imaging system.
Figure 16:
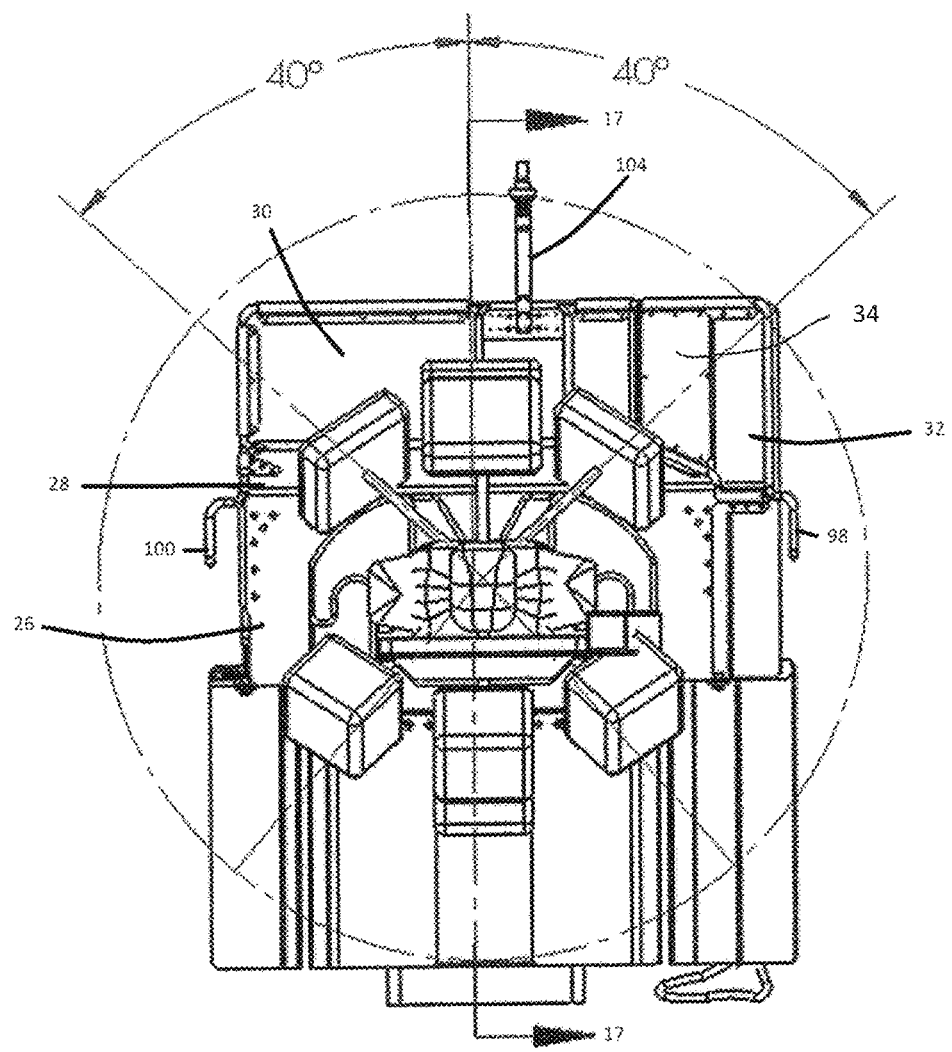
FIG. 16 is an end elevation view of the system, showing how the shield accommodates motion of the C-arm mounted imaging system.
Figure 17:
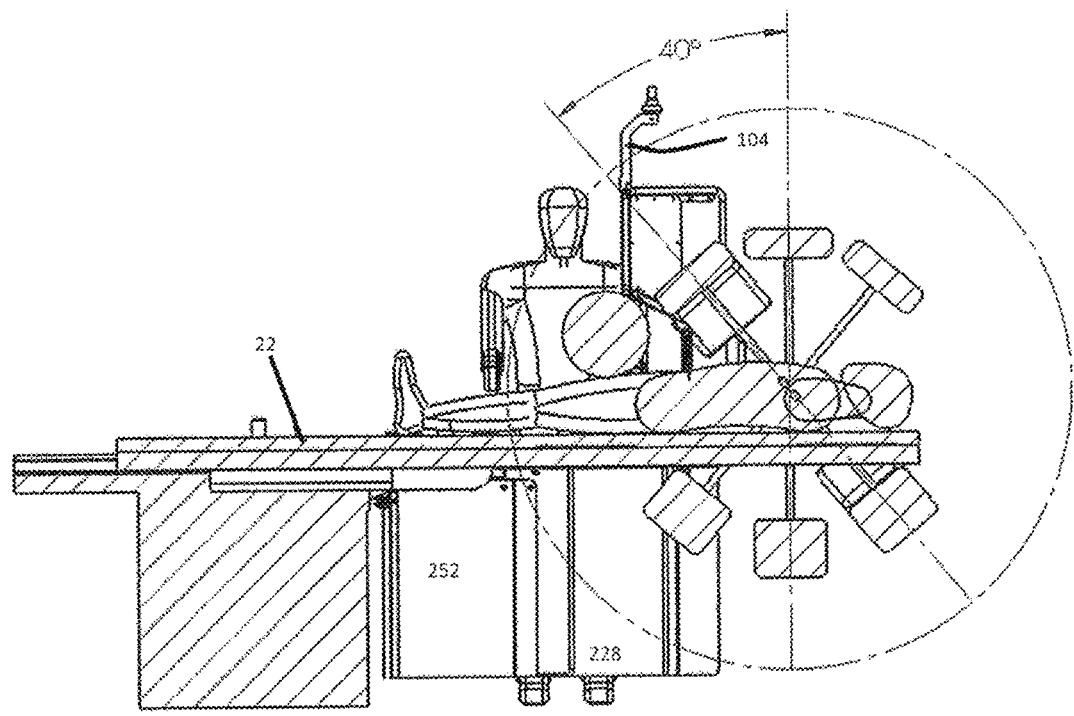
FIG. 17 is a longitudinal cross sectional view of the system, taken along the plane of line 17-17-in FIG. 16, showing how the shield accommodates motion of the C-arm mounted imaging system.
Figure 18:
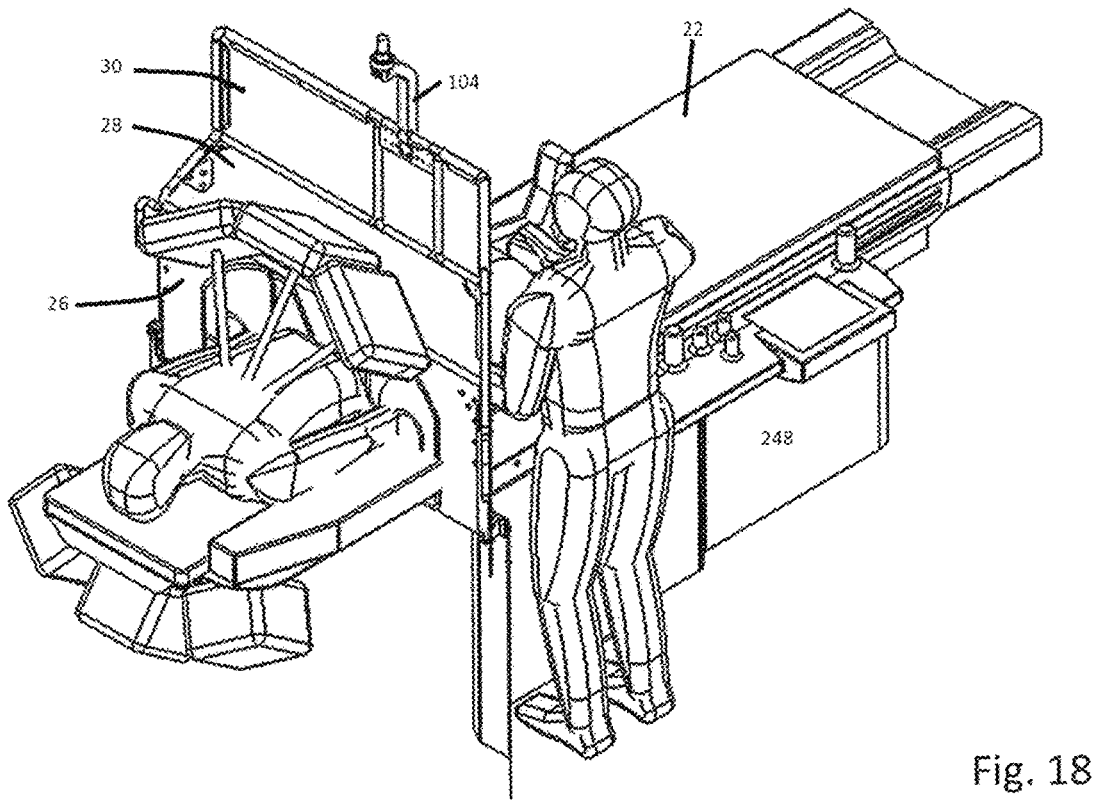
FIG. 18 is a rear perspective view of the system, showing a physician or other health care worker positioned in front of the shield, showing how the shield accommodates motion of the C-arm mounted imaging system.

Typical dimensions are shown in FIG. 14. As shown in FIG. 14, the C-arm imaging system is centered on a procedure site, approximately 12-14 inches from the barrier (13.75 inches as shown in FIG. 14). This gives the medical professional shielded access to the subject's femoral artery approximately 20-22 inches from the procedure site (21.275 inches as shown in FIG. 14), with a spacing of about 7 to 8 inches (7.375 inches as shown in FIG. 14) from the front of the shield. This gives the medical professional adequate spacing to conduct the procedure via the femoral artery (or other subject vasculature), and to visualize the site. The configuration of the intermediate and upper sections of the barrier accommodates the movement of the C-arm preferably at least 30° in the caudal direction, more preferably at least 35° in the caudal direction, and most preferably at least 40° in the caudal direction. The configuration of the sections of the barrier also accommodate the movement of the C-arm preferably at least 30° in the left and right anterior oblique directions, more preferably at least 35° in the left and right anterior oblique directions, and most preferably at least 40° in the left and right anterior oblique directions. The resiliency of the horizontal support 58 allows the barrier to flex to accommodate some movement of the C-arm imaging system at the extreme ends of its range of motion. The pivotal and hinged mounting of the bracket 104 allows additional accommodation as the barrier 24 can rotate and tilt in response to movement of the C-arm imaging system.

Further, the configuration of the barrier provides an access volume that can be visualized as a cylinder approximately 12 inches (12.5 inches as shown in FIG. 14) diameter whose central axis is 8 to 12 inches (10.25 as shown in FIG. 14) in front of the plane of the lower section of the barrier. This is generally sufficient to provide access to the patient's vasculature in front of the barrier. These are exemplary dimensions only, as the sizes of patient's can vary, but these dimensional ranges accommodate most subjects and most C-arm mounted imaging systems.

The physician remains protected from radiation generated by the imaging system 23, yet in an emergency situation, the shield 20 can be quickly moved out of the way, to provide full physician access to the subject.

As shown in FIGS. 34-38, a disposable drape 300 can be provided for the upper shield. The drape 300 preferably comprises a single ply of material folded to form a front panel 302 and a rear panel 304 that overlap the front and the back of the shield. The drape 300 has a cutout 306 with sealed or bonded margins to accommodate the recess in the lower edge of the shield. There are a plurality of adhesive tabs 308 with removable backings for securing the front and back panels 302 and 304. The corners of the front panel 302 have pockets 310 for engaging the shield, in the corners, and the corners of the rearward panel 304 have pockets for engaging the shield.

An alternative embodiment of a shield in accordance with the principles of this invention is indicated generally as 400 in FIG. 39. Shield 400 is similar in construction to the shields of the other embodiments, and corresponding parts are identified with corresponding reference numerals, and parts that are not show in FIG. 39 can be similar to the parts shown in the other embodiments.

In particular, FIG. 39 shows the use of an arm shield 402, shown in greater detail in FIG. 40. As shown in FIG. 40, arm shield 402 comprises a panel of a radiation blocking material. For example the panel can comprise multiple layers, one or more of which is radiation-blocking material such as lead. The arm shield 402 has a generally central generally circular opening 404 for receiving the subject's arm. There are one or more slits 406 extending from the perimeter of the generally circular opening 404, and least one of which (406b in FIG. 40) extends to an edge of the shield. The slits 406 allow the margins of the opening 404 to flex to accommodate subjects with different sized arms.

As shown in FIG. 40, the arm shield 402 is generally rectangular, with a top edge 408, a bottom edge 410, left and right side edges 412 and 414. Of course the arm shield 402 could be some other shape, polygonal, round, or some combination of straight and curved edges. The arm shield 402 preferably has a mounting band 416 along one edge (in this preferred embodiment, adjacent and along the top edge 408, for securing the arm shield to the shield. In this preferred embodiment the mounting band 416 is an adhesive band, which is preferably covered with a removable strip (not shown) that can be peeled expose the adhesive to temporarily secure the arm shield 402 to the shield.

The arm shield helps radiation from passing through the shield in the gaps surrounding the subject's arm, and can be used with any of the embodiments of the shield disclosed herein. If desired the arm shield can be covered with a replaceable drape.

FIG. 39 also shows the use of a side shield 440, on either side of the subject support. This side shield 440 is shown in greater detail in FIG. 41, and comprises a panel of a radiation-blocking material. For example the panel can comprise multiple layers, one or more of which is radiation-blocking material such as lead. However the panel may also be transparent and formed of a radiopaque glass or polymer. The panel preferably is rated at 0.25 mm LE, while the waist or belly shield preferably is rated at 0.5 mm L. The side shield rating of 0.25 mm LE together with the patient drape which also preferably has a rating of 0.25 mm LE, provides a total rating of 0.5 mm LE, while reducing the weight on the patient.

The side shield 440 extends generally horizontally from the sloped belly shield panel 216 described above, and can help block reflected radiation from passing between the patient support and the shield and/or passing upwardly through the patient or the patient support, and in particular helps protect the healthcare professionals hands from excessive radiation exposure.

FIG. 42 shows a mobile barrier assembly 450, that can be positioned and repositioned around the shield as necessary. The mobile barrier assembly 450 comprises a base 452 with a plurality of wheels or castors 454. Left and right struts 456 and 458 extend vertically from the base 452, and a horizontal support 460 connects the left and right struts 456 and 458. The left and right struts 456 and 458 and the horizontal support 460 support lower and upper panels 462 and 464. A frame member 466 extends from the top of the right strut 458, and together the frame and the right strut support a wing panel 470. The lower, upper and wing panels can be made of a radiation-blocking material, which can be either transparent or opaque.

A bracket 472 can extend between the left and right struts 456 and 458. The bracket 472 can engage the lower shield, and facilitate installing, removing, and transporting to the lower shield using the a mobile barrier assembly.

A leg shield 490 is shown in FIG. 43. The leg shield 490 comprises a panel of a radiation blocking material. For example the panel can comprise multiple layers, one or more of which is radiation-blocking material such as lead. The leg shield 490 has a generally central generally rounded rectangular opening 494 for receiving the subject's leg. As with the arm shield described above, there can be one or more slits extending from the perimeter of the generally rounded rectangular opening 494, and least one of which (may extends to an edge of the shield. The slits allow the margins of the opening 494 to flex to accommodate subjects with different sized legs.

As shown in FIG. 43, the leg shield 490 is generally rectangular, with a top edge 496, a bottom edge 498, left and right side edges 500 and 502. Of course the leg shield 490 could be some other shape, polygonal, round, or some combination of straight and curved edges.

The leg shield 490 helps radiation from passing through the subject's leg, and can be used with any of the embodiments of the shield disclosed herein. If desired the leg shield can be covered with a replaceable drape.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A radiation shield adapted to be disposed transversely across a subject supported on the surface of a procedure table to protect medical professionals working in a forward direction in front of the radiation shield from radiation being applied to the subject behind the radiation shield, the radiation shield comprising:
   a movable barrier positionable to extend transversely across a subject supported on the surface of an procedure table, the barrier comprising a generally vertically-oriented lower section;
   a generally forwardly sloping intermediate section; and a generally vertically-oriented upper section, forwardly offset from the plane of the lower section; and
   a side section extending outwardly and rearwardly from one side of the lower, intermediate, and upper sections;
   a recess in the lower edge of the lower section for accommodating a portion of the body of the subject on the surface of the procedure table, with portions of the lower section on each side of the recess projecting downwardly below the surface of the procedure table; and
   a plurality of flexible radiopaque flaps depending from the perimeter of the recess, for blocking radiation from penetrating the gap between the subject and the perimeter of the recess.

2. The radiation shield according to claim 1 further comprising a transparent radiopaque window in at least one of the side section and upper section of the barrier.

3. The radiation shield according to claim 1 wherein the barrier comprises a frame, and a plurality of radiopaque panels mounted on the frame.

4. The radiation shield according to claim 3 wherein the radiopaque panels are releasably mounted on the frame.

5. The radiation shield according to claim 1 wherein the height of the lower section of the barrier, and the slope of the intermediate panel are such as to provide a vertical access space above a subject on the surface of the operating that is 15⅞ inches high 8¾ inches forward of the barrier.

6. The radiation shield according to claim 1 wherein the height of the lower section of the barrier, and the slope of the intermediate panel are such that a cylinder of at least 12 inches in diameter can extend transversely across the front of the barrier, with the axis of the cylinder spaced 10 inches from the plane of the lower section.

7. The radiation shield according to claim 1 wherein the top of upper section of the barrier is at least 37 inches above the surface of the procedure table.

8. The radiation shield according to claim 1 wherein the side section extends outward from the table center at least 32 inches.

9. The radiation shield according to claim 1 wherein the barrier is enclosed in a disposable drape.

10. An operating system with shielding for protecting medical personnel working in a forward direction from radiation applied to a subject during a procedure, the system comprising:
    a procedure table;
    a C-arm supported imaging system at one end of the procedure table; and
    a shield comprising a movable barrier positionable to extend transversely across a subject being supported by an upper support system and linked to connection points on the rail system of any procedure table, the barrier comprising a generally vertically-oriented lower section;
    a generally forwardly sloping intermediate section;
    and a generally vertically-oriented upper section, forwardly offset from the plane of the lower section;
    and a side section extending outwardly and rearwardly from one side of the lower, intermediate, and upper sections;
    a recess in the lower edge of the lower section for accommodating a portion of the body of the subject on the surface of the procedure table, with portions of the lower section on each side of the recess projecting downwardly below the surface of the procedure table; and
    a plurality of flexible radiopaque flaps depending from the perimeter of the recess, for blocking radiation from penetrating the gap between the subject and the perimeter of the recess.

11. The operating system according to claim 10 wherein the barrier further comprises a transparent radiopaque window in at least one of the side section and upper section of the barrier.

12. The operating system according to claim 10 wherein the barrier further comprises a frame, and a plurality of radiopaque panels mounted on the frame.

13. The operating system according to claim 12 wherein the radiopaque panels are releasably mounted on the frame.

14. The operating system according to claim 10 wherein the height of the lower section of the barrier, and the slope of the intermediate panel are such as to provide a vertical access space above a subject on the surface of the operating that is 15⅞ inches high 8¾ inches forward of the barrier.

15. The operating system according to claim 10 wherein the height of the lower section of the barrier, and the slope of the intermediate panel are such that a cylinder of at least 12 inches in diameter can extend transversely across the front of the barrier, with the axis of the cylinder spaced 10 inches from the plane of the lower section.

16. The operating system according to claim 10 wherein the top of upper section of the barrier is at least 37 inches above the surface of the procedure table.

17. The operating system according to claim 10 wherein the side section extends outward from the table center at least 32 inches.

18. The operating system according to claim 10 wherein the barrier is enclosed in a disposable drape.

19. A radiation shield adapted to be disposed transversely across a subject supported on the surface of a procedure table to protect medical professionals working in a forward direction in front of the radiation shield from radiation being applied to the subject from a C-arm mounted imaging system behind the radiation shield, the radiation shield comprising:
    a movable barrier positional to extend transversely across a subject supported on the surface of an procedure table, the barrier comprising a generally vertically-oriented lower section;
    a generally forwardly sloping intermediate section; and
    a generally vertically-oriented upper section, forwardly offset from the plane of the lower section; and
    a side section extending outwardly and rearwardly from one side of the lower, intermediate, and upper sections;
    a recess in the lower edge of the lower section for accommodating a portion of the body of the subject on the surface of the procedure table, with portions of the lower section on each side of the recess projecting downwardly below the surface of the procedure table; and a plurality of flexible radiopaque flaps depending from the perimeter of the recess, for blocking radiation from penetrating the gap between the subject and the perimeter of the recess, the upper, intermediate, lower, and side sections being configured to accommodate the movements of the C-arm without repositioning of the shield, while providing shielded access to the patient within 21 inches from the center of the portion of the subject being imaged.

* * * * *